(12) United States Patent
Igari et al.

(10) Patent No.: US 7,294,344 B2
(45) Date of Patent: *Nov. 13, 2007

(54) SUSTAINED-RELEASE PREPARATION FOR AII ANTAGONIST, PRODUCTION AND USE THEREOF

(75) Inventors: Yasutaka Igari, Kobe (JP); Akira Saikawa, Nagaokakyo (JP); Yoshiyuki Inada, Kawanishi (JP); Shigeru Kamei, Takarazuka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 361 days.

This patent is subject to a terminal disclaimer.

(21) Appl. No.: 10/443,308

(22) Filed: May 22, 2003

(65) Prior Publication Data

US 2003/0198676 A1    Oct. 23, 2003

Related U.S. Application Data

(62) Division of application No. 09/601,986, filed on Aug. 9, 2000, now Pat. No. 6,589,547.

(30) Foreign Application Priority Data

Mar. 4, 1998  (JP) ................................. 10-52366

(51) Int. Cl.
*A61F 2/00*   (2006.01)
*A61K 9/14*   (2006.01)
*A61K 9/50*   (2006.01)

(52) U.S. Cl. ................ 424/426; 424/489; 424/499
(58) Field of Classification Search ................ 604/70; 424/468, 426, 489, 499
See application file for complete search history.

(56) References Cited

U.S. PATENT DOCUMENTS

| | | | | |
|---|---|---|---|---|
| 2,751,907 | A * | 6/1956 | Hickey ........................ | 604/60 |
| 5,225,205 | A * | 7/1993 | Orsolini ...................... | 424/489 |
| 5,721,263 | A * | 2/1998 | Inada et al. ................. | 514/381 |
| 5,958,884 | A * | 9/1999 | Kifor et al. .................. | 514/16 |
| 5,968,978 | A * | 10/1999 | Kleemann et al. ......... | 514/524 |
| 6,294,197 | B1 * | 9/2001 | Wagner et al. .............. | 424/465 |
| 6,306,826 | B1 * | 10/2001 | Ross et al. ................... | 514/12 |
| 6,589,547 | B1 * | 7/2003 | Igari et al. .................. | 424/426 |

OTHER PUBLICATIONS

Sustained Release Tablets, Feb. 2001,http://www.boomer.org/c/p1/Ch13/Ch1303.html.*

* cited by examiner

*Primary Examiner*—Sharon E. Kennedy
(74) *Attorney, Agent, or Firm*—Foley & Lardner LLP

(57) ABSTRACT

The present invention is to provide a sustained-release preparation which comprises a compound having angiotensin II antagonistic activity, its pro-drug or their salt, and a biodegradable polymer, and if necessary, a polyvalent metal, and which is highly stable and active and shows angiotensin II antagonistic activity while maintaining circadian rhythm of blood pressure for a long time.

18 Claims, No Drawings

SUSTAINED-RELEASE PREPARATION FOR AII ANTAGONIST, PRODUCTION AND USE THEREOF

This application is a divisional of U.S. patent application Ser. No. 09/601,986, filed Aug. 9, 2000, now U.S. Pat. No. 6,589,547, issued Jul. 8, 2003, which was the National Phase filing of International Patent Application No. PCT/JP99/01011, filed Mar. 3, 1999.

TECHNICAL FIELD

The present invention relates to a sustained-release preparation for a compound having angiotensin II antagonistic activity, its production method and its use as a medicine, etc.

BACKGROUND ART

The renin-angiotensin system is involved in the homeostasis to control systemic blood pressure, body fluid amount, balance among the electrolytes, etc. together with aldosterone system. The relation between renin-angiotensin and hypertension has been clarified based on the fact that angiotensin II having potent vasoconstrictive action elevates blood pressure via the angiotensin II receptors on the cellular membrane, and therefore, the antagonist of angiotensin II has been used for the treatment of hypertension caused by angiotensin. So far, drugs having angiotensin II antagonistic activity have been clinically applied by oral administration, however, said drugs are applied for symptomatic therapy which needs long term repeated administration. Therefore, due to the necessity for continuous administration, simultaneous administration with other drugs for oral administration, etc., the burden on the patient receiving oral administration of this kind of drug can not be ignored.

Moreover, there is a possibility that condition of the patient changes due to interruption of taking this kind of drug, etc. Thus, oral administration of drugs having angiotensin II antagonistic activity is not necessarily satisfactory in view of safe and reliable treatment.

In Pharmaceutical Research, 14, 887-891 (1997), there is reported a sustained-release preparation for 2-ethyl-5,7-dimethyl-3-[[2'-(1H-tetrazol-5-yl)biphenyl-4-yl]methyl]imidazo[4,5-b]pyridine having angiotensin II antagonistic activity, said preparation containing high molecular (Mw 82,000) polylactide and polyethylene-glycol 400 distearate and it is described that initial burst from the sustained-release preparation, whose drug content is about 10%, is about 20%.

In the Japanese publication translation of International patent application No. 504017/1998, a composition characterized in that a physiologically active protein together with a metal cation component is dispersed in a biocompatible polymer is disclosed.

DISCLOSURE OF INVENTION

The present invention is to provide a sustained-release preparation which comprises a high amount of a compound having angiotensin II antagonistic activity, whose initial burst is low and is capable of controlling the release rate of said compound after initial burst, and also its production and use.

The present inventors diligently made extensive studies to solve the above-mentioned problems and, as a result, they found that a sustained-release preparation comprising a compound having angiotensin II antagonistic activity and a biodegradable polymer can contain said compound in high amount, that the release rate of said compound can be controlled by the addition of a polyvalent metal compound and that by administering said preparation to spontaneous hypertension rat (SHR), the drug concentration in blood of the rat is maintained and the blood pressure of the rat can be lowered while maintaining circadian rhythm of blood pressure for a long time. The inventors made further investigations based on this finding, and developed the present invention.

More specifically, the present invention relates to (1) a sustained-release preparation which comprises a compound having angiotensin II antagonistic activity (excluding 2-ethyl-5,7-dimethyl-3-[[2'-(1H-tetrazol-5-yl)biphenyl-4-yl]methyl]imidazo[4,5-b]pyridine and a salt thereof), its pro-drug or their salt, and a biodegradable polymer;

(2) a sustained-release preparation of the above (1), wherein the compound having angiotensin II antagonistic activity is a non-peptide compound;

(3) a sustained-release preparation of the above (1), wherein the compound having angiotensin II antagonistic activity is a compound having an oxygen atom in its molecule;

(4) a sustained-release preparation of the above (1), wherein the compound having angiotensin II antagonistic activity is a compound having an ether linkage or a carbonyl group;

(5) a sustained-release preparation of the above (1), wherein the compound having angiotensin II antagonistic activity is a compound of the formula (I):

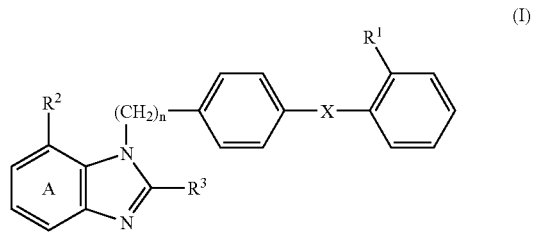

wherein $R^1$ is a group capable of forming an anion or a group capable of converting thereinto, X shows that the phenylene group and the phenyl group bind to each other directly or through a spacer having an atomic chain length of 2 or less, n is an integer of 1 or 2, the ring A is a benzene ring having an optional substitution, in addition to the group $R^2$, $R^2$ is a group capable of forming an anion or a group capable of converting thereinto, and $R^3$ is an optionally substituted hydrocarbon residue which may bind through a hetero-atom, or a salt thereof;

(6) a sustained-release preparation of the above (1), wherein the compound having angiotensin II antagonistic activity is Losartan, Eprosartan, Candesartan, Candesartan cilexetil, Valsartan, Telmisartan, Irbesartan or Tasosartan;

(7) a sustained-release preparation of the above (1), wherein the compound having angiotensin II antagonistic activity is 2-ethoxy-1-[[2'-(1H-tetrazol-5-yl)biphenyl-4-yl]methyl]benzimidazole-7-carboxylic acid or a salt thereof;

(8) a sustained-release preparation of the above (1), wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]-benzimidazole-7-carboxylate or a salt thereof;

(9) a sustained-release preparation of the above (1), wherein the compound having angiotensin II antagonistic activity is 2-ethoxy-1-[[2'-(4,5-dihydro-5-oxo-1,2,4-oxadiazol-3-yl))biphenyl-4-yl]methyl]benzimidazole-7-carboxylic acid or a salt thereof;

(10) a sustained-release preparation of the above (1), wherein the biodegradable polymer is α-hydroxycarboxylic acid polymer;

(11) a sustained-release preparation of the above (10), wherein the α-hydroxycarboxylic acid polymer is lactic acid-glycolic acid polymer;

(12) a sustained-release preparation of the above (11), wherein the molar ratio of lactic acid and glycolic acid is 100/0-40/60;

(13) a sustained-release preparation of the above (10), wherein the weight-average molecular weight of the polymer is 3,000-50,000;

(14) a sustained-release preparation of the above (1), which is for injection;

(15) a sustained-release preparation of the above (1), which further comprises a polyvalent metal;

(16) a sustained-release preparation of the above (15), wherein the polyvalent metal is zinc;

(17) a sustained-release preparation which comprises a compound having angiotensin II antagonistic activity, its pro-drug or their salt, biodegradable polymer and a polyvalent metal;

(18) a method for producing a sustained-release preparation of the above (1), which comprises removing the solvent from a solution containing a compound having angiotensin II antagonistic activity, its pro-drug or their salt, and a biodegradable polymer;

(19) a method for producing a sustained-release preparation of the above (17), which comprises removing the solvent from a solution containing a compound having angiotensin II antagonistic activity, its pro-drug or their salt, a biodegradable polymer and a polyvalent metal;

(20) a method of the above (19), wherein the polyvalent metal is zinc;

(21) a pharmaceutical composition, which comprises a sustained-release preparation of the above (1);

(22) a composition of the above (21), which is for the prevention or treatment of circulatory disease;

(23) a composition of the above (21), which is for the prevention or treatment of hypertension;

(24) a composition of the above (21), which is for the prevention or treatment of hypercardia, cardiac insufficiency, myocardial infarction, cerebral apoplexy, ischemic peripheral circulation disturbances, myocardial ischemia, vein insufficiency, progressive cardiac insufficiency after myocardial infarction, diabetic complication, diabetic retinopathy, diabetic nephropathy, nephritis, glomerulonephritis, arteriosclerosis, angiohypertrophy, vascular hypertrophy or obstruction after intervention, vascular reobstruction after bypass surgery, hyperaldosteronism, glomerulosclerosis, renal insufficiency, glaucoma, intraocular high tension, hyperlipemia, angina pectoris, aneurysm, coronary arteriosclerosis, cerebral arteriosclerosis, peripheral arteriosclerosis, thrombosis, disease of central nervous system, Alzheimer's disease, deficiency of memory, depression, amnesia, senile dementia, sensory disturbances, multiple system organ failure, a disease due to endothelial dysfunction or scleroderma, or the prevention or amelioration of anxiety neurosis, catatonia, indisposition or dyspeptic symptoms; etc.

In the present specification, the angiotensin II antagonistic activity is to inhibit competitively or non-competitively binding of angiotensin II to the angiotensin II receptors on the cellular membrane so as to reduce potent vasoconstrictive action or vascular smooth muscle proliferation action induced by angiotensin II and to ameliorate the symptom of hypertension.

The compound having angiotensin II antagonistic activity to be used for the present invention may be either a peptide compound or a non-peptide compound. In view of the advantage of long action, a non-peptide compound having angiotensin II antagonistic activity is preferable. As the compound having angiotensin II antagonistic activity, a compound having an oxygen atom in its molecule is preferable, a compound having an ether linkage or a carbonyl group (said carbonyl group may form a hydroxy group by resonance) is more preferable, a compound having an ether linkage or a ketone derivative is further preferable, and in particular, an ether derivative is preferable.

Any non-peptide compound having angiotensin II antagonistic activity can be used for the present invention. Examples of said compounds include imidazole derivatives disclosed in Japanese Patent Unexamined Publication No. 71073/1981, Japanese Patent Unexamined Publication No. 71074/1981, Japanese Patent Unexamined Publication No. 98270/1982, Japanese Patent Unexamined Publication No. 157768/1983, U.S. Pat. No. 4,355,040, U.S. Pat. No. 4,340,598, etc.; modified imidazole derivatives disclosed in EP-253310, EP-291969, EP-324377, EP-403158, WO-9100277, Japanese Patent Unexamined Publication No. 23868/1988, Japanese Patent Unexamined Publication No. 117876/1989, etc.; pyrrole, pyrazole and triazole derivatives disclosed in U.S. Pat. No. 5,183,899, EP-323841, EP-409332, Japanese Patent Unexamined Publication No. 287071/1989, in etc.; benzimidazole derivatives disclosed in U.S. Pat. No. 4,880,804, EP-0392317, EP-0399732, EP-0400835, EP-425921, EP-459136, Japanese Patent Unexamined Publication No. 63264/1991, etc.; azaindene derivatives disclosed in EP-399731, etc.; pyrimidone derivatives disclosed in EP-407342, etc.; quinazoline derivatives disclosed in EP-411766, etc.; xanthine derivatives disclosed in EP-430300, etc.; fused imidazole derivatives disclosed in EP-434038, etc.; pyrimidinedione derivatives disclosed in EP-442473, etc.; thienopyridone derivatives disclosed in EP-443568, etc.; heterocyclic compounds disclosed in EP-445811, EP-483683, EP-518033, EP-520423, EP-588299, EP-603712, etc. In addition, their representative compounds are described in Journal of Medicinal Chemistry, Vol. 39, No. 3, pages 625-656 (1996). As the non-peptide compound having angiotensin II antagonistic activity, any one in addition to the compounds described in the above-mentioned references can be employed as far as it has angiotensin II antagonistic activity. Among others, Losartan (DuP753), Eprosartan (SK&F108566), Candesartan cilexetil (TCV-116), Valsartan (CGP-48933), Telmisartan (BIBR277), Irbesartan (SR47436) Tasosartan (ANA-756), their active metabolites (Candesartan, etc.), etc. are preferable.

Preferred examples of the non-peptide compound having angiotensin II antagonistic activity include, for example, a benzimidazole derivative of the formula (I):

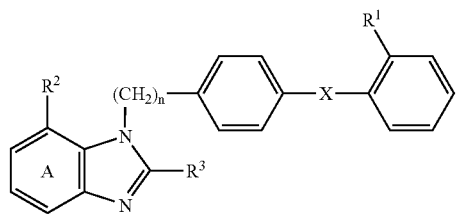

wherein $R^1$ is a group capable of forming an anion or a group capable of converting thereinto, X shows that the phenylene group and the phenyl group bind to each other directly or through a spacer having an atomic chain length of 2 or less, n is an integer of 1 or 2, the ring A is a benzene ring having an optional substitution, in addition to the group $R^2$, $R^2$ is a group capable of forming an anion or a group capable of converting thereinto, and $R^3$ is an optionally substituted hydrocarbon residue which may bind through a hetero-atom (preferably, an optionally substituted hydrocarbon residue which binds through an oxygen atom), etc., or a salt thereof.

In the above formula (I), the group capable of forming an anion (a group having a hydrogen atom capable of leaving as a proton) as $R^1$ include, for example, (1) a carboxyl group, (2) a tetrazolyl group, (3) a trifluoromethanesulfonic acid amido group (—$NHSO_2CF_3$), (4) a phosphono group, (5) a sulfo group, (6) an optionally substituted 5- to 7-membered (preferably 5- to 6-membered) monocyclic heterocyclic ring residue which contains one or more of N, S and O, etc.

Examples of the above "optionally substituted 5- to 7-membered (preferably 5- to 6-membered) monocyclic heterocyclic ring residue which contains one or more of N, S and O" include

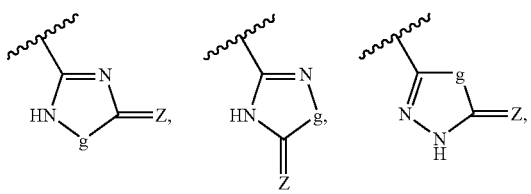

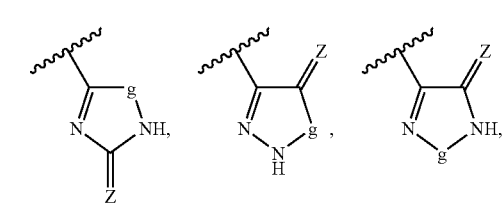

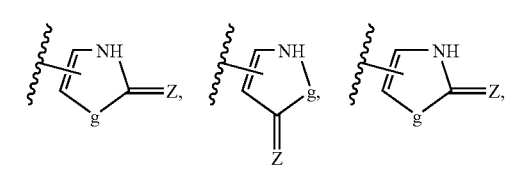

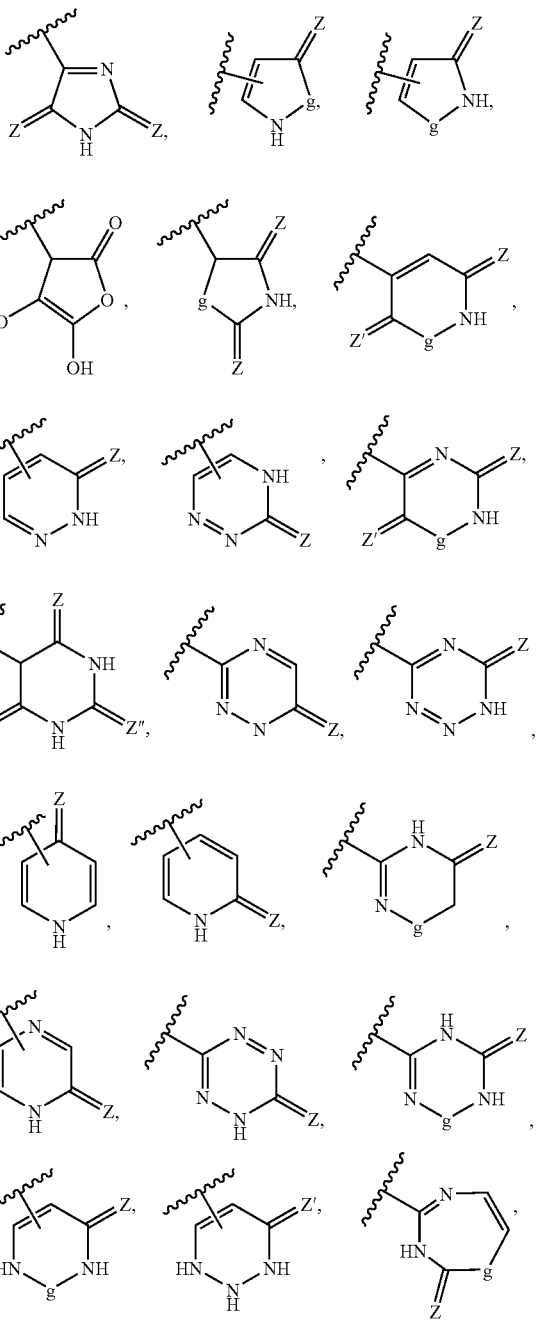

etc. The chemical bond between the heterocyclic ring residue represented by $R^1$ and the phenyl group to which said heterocyclic ring residue binds may be a carbon-carbon bond as shown above, or a nitrogen-carbon bond via one of the several nitrogen atoms when the symbol g is —NH—, etc. in the above formulas.

For example, when $R^1$ is represented by the formula:

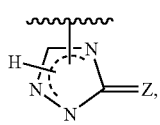

its specific embodiments are

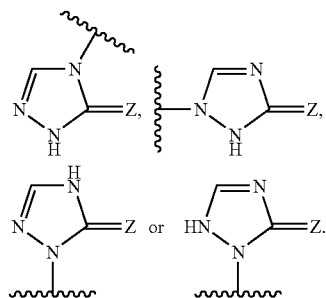

Other examples of $R^1$ binding through a nitrogen atom include

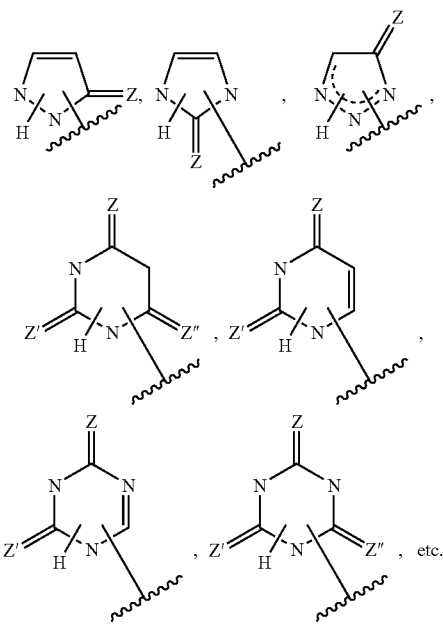

In the above formula, g is —$CH_2$—, —NH—, —O— or —$S(O)_m$—; >=Z, >=Z' and >=Z" are independently a carbonyl group, a thiocarbonyl group or an optionally oxidized sulfur atom (e.g., S, S(O), $S(O)_2$, etc.) (preferably a carbonyl group or a thiocarbonyl group, more preferably carbonyl group); and m is an integer of 0, 1 or 2.

Preferred examples of the heterocyclic ring residue represented by $R^1$ include a heterocyclic ring residue simultaneously having —NH— or —OH group as proton donor and a carbonyl group, a thiocarbonyl group, a sulfinyl group, etc. as proton aceptor, such as an oxadiazolone ring, an oxadiazolothione ring or an thiadiazolone ring, etc.

While the heterocyclic ring residue represented by R may form a condensed ring by connecting the substituents on the heterocyclic ring, it is a preferably 5- to 6-membered ring residue, more preferably 5-membered ring residue.

Preferred examples of the heterocyclic ring residue represented by $R^1$ include a group of the formula:

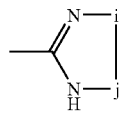

wherein i is —O— or —S—, j is >=O, >=S or >=S(O)m, and m is as defined above (preferably, 4,5-dihydro-5-oxo-1,2,4-oxadiazol-3-yl, 4,5-dihydro-5-thioxo-1,2,4-oxadiazol-3-yl, 4,5-dihydro-5-oxo-1,2,4-thiadiazol-3-yl; more preferably, 4,5-dihydro-5-oxo-1,2,4-oxadiazol-3-yl).

The above-mentioned heterocyclic ring residue ($R^1$) have the following tautomeric isomers. For example, in

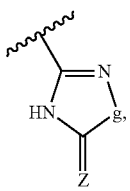

when Z is 0 and g is 0,

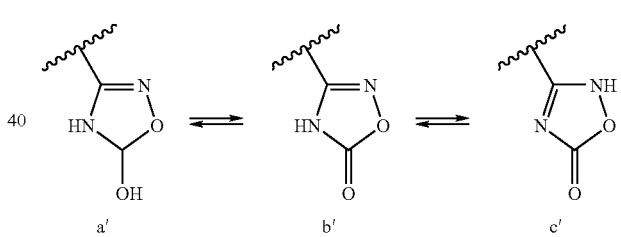

the three tautomeric isomers a', b' and c' exist and a group of the formula:

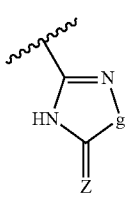

include all of the above a', b' and c'.

The group capable of forming an anion as $R^1$ may be protected by an optionally substituted lower ($C_{1-4}$) alkyl group, an acyl group (e.g., lower ($C_{2-5}$) alkanoyl, benzoyl, etc.), etc. at its possible position.

Examples of the optionally substituted lower ($C_{1-4}$) alkyl group include (1) a lower ($C_{1-4}$) alkyl group optionally substituted with one to three phenyl groups which may have halogen atom, nitro, lower ($C_{1-4}$) alkyl, lower ($C_{1-4}$) alkoxy, etc. (e.g., methyl, triphenylmethyl, p-methoxybenzyl, p-nitrobenzyl, etc.); (2) a lower ($C_{1-4}$) alkoxy-lower ($C_{1-4}$ alkyl group (e.g., methoxymethyl, ethoxymethyl, etc.); (3) a group of the formula: —CH($R^4$)—OCOR$^5$ wherein $R^4$ is (a) a hydrogen, (b) a straight or branched lower $C_{1-6}$ alkyl group (e.g., methyl, ethyl, n-propyl, isopropyl, n-butyl, isobutyl, t-butyl, n-pentyl, isopentyl, neopentyl, etc.), (c) a straight or branched lower $C_{2-6}$ alkenyl group or (d) a $C_{3-8}$ cycloalkyl group (e.g., cyclopentyl, cyclohexyl, cycloheptyl, etc.), and $R^5$ is (a) a straight or branched lower $C_{1-6}$ alkyl group (e.g., methyl, ethyl, n-propyl, isopropyl, n-butyl, isobutyl, sec-butyl, t-butyl, n-pentyl, isopentyl, neopentyl, etc.), (b) a straight or branched lower $C_{2-6}$ alkenyl group, (c) a lower $C_{1-3}$ alkyl group substituted with a $C_{3-8}$ cycloalkyl group (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyl, p-chlorobenzyl, phenethyl, cyclopentylmethyl, cyclohexylmethyl, etc., (d) a lower $C_{2-3}$ alkenyl group substituted with a $C_{3-8}$ cycloalkyl or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as cinnamyl, etc. having an alkenyl moiety such as vinyl, propenyl, allyl, isopropenyl, etc., (e) an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as phenyl, p-tolyl, naphthyl, etc., (f) a straight or branched lower $C_{1-6}$ alkoxy group (e.g., methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g., allyloxy, isobutenyloxy, etc.), (h) a $C_{3-8}$ cycloalkyloxy group (e.g., cyclopentyloxy, cyclohexyloxy, cycloheptyloxy, etc.), (i) a lower $C_{1-3}$ alkoxy group substituted with a $C_{3-8}$ cycloalkyl (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyloxy, phenethyloxy, cyclopentylmethoxy, cyclohexylmethoxy, etc. having an alkoxy moiety such as methoxy, ethoxy, n-propoxy, isopropoxy, etc., etc.), (j) a lower $C_{2-3}$ alkenyloxy group substituted with a $C_{3-8}$ cycloalkyl (e.g., cyclopentyl, cyclohexyl, cycloheptyl, etc.) or an optionally substituted aryl group (e.g., a phenyl group or a naphthyl group, etc., optionally having a halogen atom, a nitro, a lower ($C_{1-4}$) alkyl, a lower ($C_{1-4}$) alkoxy, etc.) such as cinnamyloxy, etc. having an alkenyloxy moiety such as vinyloxy, propenyloxy, allyloxy, isopropenyloxy, etc. or (k) an optionally substituted aryloxy group (e.g., a phenoxy group, a naphthoxy group, etc., optionally having a halogen atom, a nitro, a lower ($C_{1-4}$) alkyl, a lower ($C_{1-4}$) alkoxy, etc.) such as phenoxy, p-nitrophenoxy, naphthoxy, etc.; etc.

The group capable of forming an anion as $R^1$ may be substituted, in addition to the above protective group such as an optionally substituted lower ($C_{1-4}$) alkyl group or an acyl group (e.g., lower ($C_{2-5}$) alkanoyl, benzoyl, etc.), etc., with an optionally substituted lower ($C_{1-4}$) alkyl group (e.g. an optionally substituted lower ($C_{1-4}$) alkyl group similar to the "optionally substituted lower ($C_{1-4}$) alkyl group" exemplified as a protective group for the above group capable of forming an anion as $R^1$), a halogen atom, a nitro, a cyano, a lower ($C_{1-4}$) alkoxy, an amino optionally substituted with 1 to 2 lower ($C_{1-4}$) alkyl groups, etc., at the possible position.

In the above formula, the group convertible into the group capable of forming an anion (a group having a hydrogen atom capable of leaving as proton) as $R^1$ may be a group convertible into a group capable of forming an anion under biological or physiological conditions (for example, in vivo reaction, etc. such as oxidation, reduction, hydrolysis, etc. by in vivo enzyme, etc.) [so called pro-drug], or the group convertible into a group capable of forming an anion represented by $R^1$ may be a group chemically convertible into a group capable of forming an anion, such as cyano, N-hydroxycarbamimidoyl group (—C(=N—OH)—NH$_2$), a group selected from the class consisting of (1) a carboxyl group, (2) a tetrazolyl group, (3) a trifluoromethanesulfonic acid amido group (—NHSO$_2$CF$_3$), (4) a phosphono group, (5) a sulfo group and (6) an optionally substituted monocyclic 5- to 7-membered (preferably 5- to 6-membered) monocyclic heterocyclic ring residue which contains one or more of N, S and O, each of which is protected with an optionally substituted lower ($C_{1-4}$) alkyl group or an acyl group, etc. [so called synthetic intermediate].

As the group $R^1$, (1) carboxyl, tetrazolyl or 4,5-dihydro-5-oxo-1,2,4-oxadiazol-3-yl (preferably, tetrazolyl), each of which may be protected with an optionally substituted lower ($C_{1-4}$) alkyl (e.g., methyl, triphenylmethyl, methoxymethyl, ethoxymethyl, p-methoxybenzyl, p-nitrobenzyl, etc.) or an acyl group (e.g., lower ($C_{2-5}$) alkanoyl, benzoyl, etc.) or (2) cyano or N-hydroxycarbamimidoyl (preferably cyano) is preferable.

In the above formula, X shows that the phenylene group is bonded to the adjacent phenyl group directly or through a spacer with an atomic chain of 2 or less (preferably directly). Examples of the spacer with an atomic chain of 2 or less include any divalent chain in which the number of atoms constituting the straight chain is 1 or 2 and which may have a side chain, and specifically lower ($C_{1-4}$) alkylene in which the number of atoms constituting the straight chain is 1 or 2, —CO—, —O—, —S—, —NH—, —CO—NH—, —O—CH$_2$—, —S—CH$_2$—, —CH=CH—, etc.

In the above formula, n is an integer of 1 or 2 (preferably 1).

In the above formula, the ring A may have, in addition to the group $R^2$, another substituent, for example, (1) halogen (e.g., F, Cl, Br, etc.), (2) cyano, (3) nitro, (4) an optionally substituted lower ($C_{1-4}$) alkyl, (5) a lower ($C_{1-4}$) alkoxy, (6) an optionally substituted amino group (e.g., amino, N-lower ($C_{1-4}$) alkylamino (e.g., methylamino, etc.), N,N-di-lower ($C_{1-4}$) alkylamino (e.g., dimethylamino, etc.), N-arylamino (e.g., phenylamino, etc.), alicyclic amino (e.g., morpholino, piperidino, piperazino, N-phenylpiperazino, etc.), etc.), (7) a group of the formula: —CO—D' wherein D' is a hydroxy group or a lower ($C_{1-4}$) alkoxy whose alkyl moiety may be substituted with a hydroxy group, a lower ($C_{1-4}$) alkoxy, a lower ($C_{2-6}$) alkanoyloxy (e.g., acetoxy, pivaloyloxy, etc.), a lower ($C_{1-6}$) alkoxy-carbonyloxy (e.g., methoxycarbonyloxy, ethoxycarbonyloxy, etc.) or a lower ($C_{3-6}$) cycloalkoxycarbonyloxy (e.g., cyclohexyloxycarbonyloxy, etc.), or (8) tetrazolyl, trifluoromethanesulfonic acid amide group, phosphono group or sulfo group, each of which may be protected with an optionally substituted lower ($C_{1-4}$) alkyl ("an optionally substituted lower ($C_{1-4}$) alkyl group" similar to that exemplified as a protective group for the above group capable of forming an anion represented by $R^1$, etc.) or acyl (e.g., lower ($C_{2-5}$) alkanoyl, benzoyl, etc.), etc.

Of these substituents, one or two may simultaneously be present at any possible position on the benzene ring, in addition to the group $R^2$, and preferred examples of the substituents for the benzene ring represented by A include an optionally substituted lower ($C_{1-4}$) alkyl (e.g., a lower ($C_{1-4}$) alkyl, etc. optionally substituted with a hydroxy group, a carboxyl group, a halogen, etc.), a halogen etc.

As the ring A, a benzene ring having no substituent in addition to the group $R^2$ is preferable.

In the above formula, examples of the group capable of forming an anion (a group having a hydrogen atom capable of leaving as proton) as $R^2$ include (1) an optionally esterified or amidated carboxyl group, (2) a tetrazolyl group, (3) a trifluoromethanesulfonic acid amido group ($-NHSO_2CF_3$), (4) a phosphono group, (5) a sulfo group, etc., each of which may be protected with an optionally substituted lower alkyl group (e.g. an optionally substituted lower ($C_{1-4}$) alkyl group similar to the "optionally substituted lower ($C_{1-4}$) alkyl group" exemplified as a protective group for the above group capable of forming an anion as $R^1$) or an acyl group (e.g., lower ($C_{2-5}$) alkanoyl, benzoyl, etc.), or any one of the groups capable of converting thereinto under biological or physiological conditions (for example, in vivo reaction, etc. such as oxidation, reduction, hydrolysis, etc. by in vivo enzyme, etc.), or chemically.

Examples of the optionally esterified or amidated carboxyl as $R^2$ include a group of the formula: $-CO-D$ wherein D is (1) a hydroxy group, (2) an optionally substituted amino (for example, amino, N-lower ($C_{1-4}$) alkylamino, N,N-di-lower ($C_{1-4}$) alkylamino, etc.) or (3) an optionally substituted alkoxy [e.g., (i) a lower ($C_{1-6}$) alkoxy group whose alkyl moiety is optionally substituted with a hydroxy group, an optionally substituted amino (e.g., amino, N-lower ($C_{1-4}$) alkylamino, N,N-di-lower ($C_{1-4}$) alkylamino, piperidino, morpholino, etc.), a halogen, a lower ($C_{1-6}$) alkoxy, a lower ($C_{1-6}$) alkylthio, a lower ($C_{3-8}$) cycloalkoxy or an optionally substituted dioxolenyl (e.g., 5-methyl-2-oxo-1,3-dioxolen-4-yl, etc.), or (ii) a group of the formula: $-O-CH(R^6)-OCOR$ wherein $R^6$ is (a) a hydrogen, (b) a straight or branched $C_{1-6}$ lower alkyl group (e.g., methyl, ethyl, n-propyl, isopropyl, n-butyl, isobutyl, t-butyl, n-pentyl, isopentyl, neopentyl, etc.), (c) a straight or branched $C_{2-6}$ lower alkenyl group or (d) a $C_{3-8}$ cycloalkyl group (e.g., cyclopentyl, cyclohexyl, cycloheptyl, etc.), and $R^7$ is (a) a straight or branched $C_{1-6}$ lower alkyl group (e.g., methyl, ethyl, n-propyl, isopropyl, n-butyl, isobutyl, sec-butyl, t-butyl, n-pentyl, isopentyl, neopentyl, etc.), (b) a straight or branched $C_{3-6}$ lower alkenyl group, (c) a lower $C_{1-3}$ alkyl group substituted with a $C_{3-8}$ cycloalkyl group (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyl, p-chlorobenzyl, phenethyl, cyclopentylmethyl, cyclohexylmethyl, etc., (d) a lower $C_{2-3}$ alkenyl group substituted with a $C_{3-8}$ cycloalkyl or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as cinnamyl, etc. having an alkenyl moiety such as vinyl, propenyl, allyl, isopropenyl, etc., (e) an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as phenyl, p-tolyl, naphthyl, etc., (f) a straight or branched lower $C_{1-6}$ alkoxy group (e.g., methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g., allyloxy, isobutenyloxy, etc.), (h) a $C_{3-8}$ cycloalkyloxy group (e.g., cyclopentyloxy, cyclohexyloxy, cycloheptyloxy, etc.), (i) a lower $C_{1-3}$ alkoxy group substituted with a $C_{3-8}$ cycloalkyl (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyloxy, phenethyloxy, cyclopentylmethoxy, cyclohexylmethoxy, etc. having an alkoxy moiety such as methoxy, ethoxy, n-propoxy, isopropoxy, etc., etc.), (j) a lower $C_{2-3}$ alkenyloxy group substituted with a $C_{3-8}$ cycloalkyl (e.g., cyclopentyl, cyclohexyl, cycloheptyl, etc.) or an optionally substituted aryl group (e.g., a phenyl group or a naphthyl group, etc., optionally having a halogen atom, a nitro, a lower ($C_{1-4}$) alkyl, a lower ($C_{1-4}$) alkoxy, etc.) such as cinnamyloxy, etc. having an alkenyloxy moiety such as vinyloxy, propenyloxy, allyloxy, isopropenyloxy, etc. or (k) an optionally substituted aryloxy group (e.g., a phenoxy group, a naphthoxy group, etc., optionally having a halogen atom, a nitro, a lower ($C_{1-4}$) alkyl, a lower ($C_{1-4}$) alkoxy, etc.) such as phenoxy, p-nitrophenoxy, naphthoxy, etc.], etc.

As $R^2$, an optionally esterified carboxyl is preferable, and its specific examples include $-COOH$ and a salt thereof, $-COOMe$, $-COOEt$, $-COOtBu$, $-COOPr$, pivaloyloxymethoxy-carbonyl, 1-(cyclohexyloxycarbonyloxy)ethoxycarbonyl, 5-methyl-2-oxo-1,3-dioxolen-4-yl-methoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)-ethoxycarbonyl, 1-(isobutyryloxy)ethoxycarbonyl, cyclohexylcarbonyloxymethoxycarbonyl, benzoyloxy-methoxycarbonyl, cinnamyloxycarbonyl, cyclopentyl-carbonyloxymethoxycarbonyl, etc. The group $R^2$ may be any one of the groups capable of forming an anion under biological or physiological conditions (for example, in vivo reaction, etc. such as oxidation, reduction, hydrolysis, etc. by in vivo enzyme, etc.), the groups capable of chemically forming an anion (e.g., $COO-$, its derivative, etc.) or the groups capable of converting thereinto. The group $R^2$ may be a carboxyl group or its pro-drug.

Preferred examples of the group $R^2$ include a group of the formula: $-CO-D$ wherein D is (1) a hydroxy group or (2) a lower ($C_{1-4}$) alkoxy whose alkyl moiety is optionally substituted with a hydroxy group, an amino, a halogen a lower ($C_{2-6}$) alkanoyloxy (e.g., acetoxy, pivaloyloxy etc.), a lower ($C_{3-8}$) cycloalkanoyloxy, a lower ($C_{1-6}$) alkoxy-carbonyloxy (e.g., methoxycarbonyloxy, ethoxycarbonyloxy, etc.), a lower ($C_{3-8}$) cycloalkoxycarbonyloxy (e.g., cyclohexyloxycarbonyloxy, etc.), a lower ($C_{1-4}$) alkoxy or a lower ($C_{3-8}$) cycloalkoxy. Among others, an esterified carboxyl with a lower ($C_{1-4}$) alkyl (preferably, methyl or ethyl) is preferable.

In the above formula, examples of the "hydrocarbon residue" in the "optionally substituted hydrocarbon residue which may bind through a hetero-atom" represented by $R^3$ include (1) an alkyl group, (2) an alkenyl group, (3) an alkynyl group, (4) an cycloalkyl group, (5) an aryl group, (6) an aralkyl group, etc. Among others, an alkyl group, an alkenyl group and a cycloalkyl group are preferable.

Examples of the alkyl group of the above mentioned (1) include straight or branched lower alkyl group having about 1-8 carbon atoms such as methyl, ethyl, propyl, isopropyl, butyl, isobutyl, sec-butyl, t-butyl, pentyl, i-pentyl, hexyl, heptyl, octyl, etc.

Examples of the alkenyl group of the above mentioned (2) include straight or branched lower alkenyl group having about 2-8 carbon atoms such as vinyl, propenyl, 2-butenyl, 3-butenyl, isobutenyl, 2-octenyl, etc.

Examples of the alkynyl group of the above mentioned (3) include straight or branched lower alkynyl group having about 2-8-carbon atoms such as ethynyl, 2-propynyl, 2-butynyl, 2-pantynyl, 2-octynyl, etc.

Examples of the cycloalkyl group of the above (4) include a lower cycloalkyl having about 3-6 carbon atoms, such as cyclopropyl, cyclobutyl, cyclopentyl, cyclohexyl, etc.

Each of the above-mentioned alkyl group, alkenyl group, alkenyl group and cycloalkyl group may be substituted with hydroxy group, an optionally substituted amino group (e.g., amino, N-lower ($C_{1-4}$) alkylamino, N,N-di-lower ($C_{1-4}$) alkylamino, etc.), halogen, lower ($C_{1-4}$) alkoxy group, lower ($C_{1-4}$) alkylthio group, etc.

Examples of the aralkyl group of the above (5) include a phenyl-lower ($C_{1-4}$) alkyl, etc., such as benzyl, phenethyl, etc.

Examples of the aryl group of the above (6) include phenyl, etc.

Each of the above-mentioned aralkyl group and aryl group may be substituted, at any possible position on the benzene ring, with a halogen (e.g., F, Cl, Br, etc.), a nitro, an optionally substituted amino group (e.g., amino, N-lower ($C_{1-4}$) alkylamino, N,N-di-lower ($C_{1-4}$) alkylamino, etc.), a lower ($C_{1-4}$) alkoxy (e.g., methoxy, ethoxy, etc.), a lower ($C_{1-4}$) alkylthio (e.g., methylthio, ethylthio, etc.), a lower ($C_{1-4}$) alkyl (e.g., methyl, ethyl, etc.), etc.

Preferred examples of the "optionally substituted hydrocarbon residue" in the "optionally substituted hydrocarbon residue which may bind through a hetero-atom" represented by $R^3$ include an optionally substituted alkyl or alkenyl group (e.g., a lower ($C_{1-5}$) alkyl or a lower ($C_{2-5}$) alkenyl group, each of which may be substituted with a hydroxy group, an amino group, a halogen, a lower ($C_{1-4}$) alkoxy group, etc.). Among others, a lower ($C_{1-5}$) alkyl (more preferably, ethyl) is preferable.

Preferred examples of the "hetero-atom" in the "optionally substituted hydrocarbon residue which may bind through a hetero-atom" represented by $R^3$ include —O—, —S(O)m— [m is an integer of 0-2], —NR'-[R' is a hydrogen atom or a lower ($C_{1-4}$) alkyl], etc. Among others, —O— is preferable.

Among others, as $R^3$, a lower ($C_{1-5}$) alkyl or a lower ($C_{2-5}$) alkenyl group, each of which may be substituted with a substituent selected from the class consisting of a hydroxy group, an amino group, a halogen and a lower ($C_{1-4}$) alkoxy group and which may bind through —O—, —S(O)m— [m is an integer of 0-2] or —NR'-[R' is a hydrogen atom or a lower ($C_{1-4}$) alkyl], etc. are preferable and a lower ($C_{1-5}$) alkyl or lower ($C_{1-5}$) alkoxy (in particular, ethoxy) is more preferable.

Among the non-peptide compounds having angiotensin II antagonistic activity and represented by the formula (I), a benzimidazole-7-carboxylic acid derivative of the formula (I'):

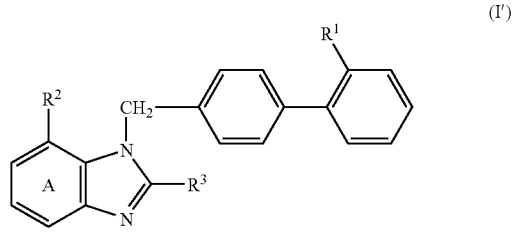

wherein $R^1$ is (1) carboxyl group, (2) tetrazolyl group or (3) a group of the formula:

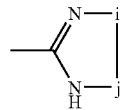

wherein i is —O— or —S—, j is >=O, >=S or >=S(O)m, and m is as defined above; the ring A is a benzene ring having an optional substituent selected from the class consisting of an optionally substituted lower ($C_{1-4}$) alkyl (e.g., a lower ($C_{1-4}$) alkyl optionally substituted with a hydroxy group, a carboxyl group, a halogen, etc.) and a halogen, in addition to the group $R^2$ (preferably, a benzene ring having no substituent in addition to the group $R^2$); $R^2$ is a group of the formula: —CO—D wherein D is (1) a hydroxy group or (2) a lower ($C_{1-4}$) alkoxy whose alkyl moiety may be substituted with a hydroxy group, an amino, a halogen, a lower ($C_{2-6}$) alkanoyloxy (e.g., acetoxy, pivaloyloxy, etc.), a lower ($C_{3-8}$) cycloalkanoyloxy, a lower ($C_{1-6}$) alkoxycarbonyloxy (e.g., methoxycarbonyloxy, ethoxy-carbonyloxy, etc.), a lower ($C_{3-8}$) cycloalkoxycarbonyloxy (e.g., cyclohexyloxycarbonyloxy, etc.), a lower ($C_{1-4}$) alkoxy or a lower ($C_{3-8}$) cycloalkoxy; $R^3$ is a lower ($C_{1-5}$) alkyl or a lower ($C_{2-5}$) alkenyl group, each of which may bind through —O—, —S(O)m— [m is an integer of 0-2] or —NR'-[R' is a hydrogen atom or a lower ($C_{1-4}$) alkyl] and which may be substituted with a substituent selected from the class consisting of a hydroxy group, an amino group, a halogen and a lower ($C_{1-4}$) alkoxy group (preferably, a lower ($C_{1-5}$) alkyl or a lower ($C_{1-5}$) alkoxy; more preferably, ethoxy), etc. or a pharmaceutically acceptable salt thereof is preferable.

Among others, 2-ethoxy-1-[[2'-(1H-tetrazol-5-yl)biphenyl-4-yl]methyl]benzimidazole-7-carboxylic acid [Candesartan], 1-(cyclohexyloxycarbonyloxy)ethyl 2-ethoxy-1-[[2'-(1H-tetrazol-5-yl)biphenyl-4-yl]methyl]-benzimidazole-7-carboxylate [Candesartan cilexetil], pivaloyloxymethyl 2-ethoxy-1-[[2'-(1H-tetrazol-5-yl)biphenyl-4-yl]methyl]benzimidazole-7-carboxylate, 2-ethoxy-1-[[2'-(4,5-dihydro-5-oxo-1,2,4-oxadiazol-3-yl)biphenyl-4-yl]methyl]benzimidazole-7-carboxylic acid, etc. or a salt thereof are preferable.

The above mentioned benzimidazole derivative can be produced by known methods described in, for example, EP-425921, EP-459136, EP-553879, EP-578125, EP-520423, EP-668272, etc. or a method analogous thereto. When Candesartan cilexetil is used for the present invention, a stable C-type crystal described in EP-459136 is preferably used.

The compound having angiotensin II antagonistic activity or a pro-drug thereof may be a distinct entity or in the form of any possible pharmaceutically acceptable salts thereof. Examples of said salts include a salt with inorganic bases (e.g., alkaline metals such as sodium, potassium, etc.; alkaline earth metals such as calcium, magnesium, etc.; transition metal such as zinc, iron, copper, etc.; etc.); organic bases (e.g., organic amines such as trimethylamine, triethylamine, pyridine, picoline, ethanolamine, diethanolamine, triethanolamine, dicyclohexylamine, N,N'-dibenzylethylenediamine, etc.; basic amino acids such as arginine, lysine, ornithine, etc.; etc.); etc., when said compound having angiotensin II antagonistic activity has an acidic group such as a carboxyl group, etc.; and a salt with inorganic acids or organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); acidic amino acids such as aspartic acid, glutamic acid, etc.; etc., when said compound having angiotensin II antagonistic activity has a basic group such as an amino group, etc.

The pro-drug of the compound having angiotensin II antagonistic activity [hereinafter, referred to as AII antagonist] means a compound which is converted to AII antagonist under physiological conditions or with a reaction due to an enzyme, an gastric acid, etc. in the living body, that is, a compound which is converted to AII antagonist with oxidation, reduction, hydrolysis, etc. according to an enzyme; a compound which is converted to AII antagonist with gastric acid, etc.; etc.

Examples of the pro-drug of the AII antagonist include a compound wherein an amino group of the AII antagonist is substituted with acyl, alkyl, phosphoric acid, etc. (e.g. a compound wherein an amino group of the AII antagonist is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of the AII antagonist is substituted with acyl, alkyl, phosphoric acid, boric acid, etc. (e.g. a compound wherein an hydroxy group of the AII antagonist is substituted with acetyl, palmitoyl, propanoyl, pivaloyl, succinyl, fumaryl, alanyl, dimethylaminomethylcarbonyl, etc.); a compound wherein a carboxyl group of the AII antagonist is modified with ester, amide, etc. (e.g. a compound wherein a carboxyl group of the AII antagonist is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drugs can be produced by per se known methods from the AII antagonist.

The pro-drug of the AII antagonist may be a compound which is converted into the AII antagonist under the physiological conditions as described in "Pharmaceutical Research and Development", Vol. 7 (Drug Design), pages 163-198 published in 1990 by Hirokawa Publishing Co. (Tokyo, Japan).

Also, the AII antagonist may be hydrated.

Examples of the biodegradable polymer to be used in the present invention include a polymer, a copolymer, their ester, or a mixture thereof which is synthesized from one or more of α-hydroxycarboxylic acids (e.g., glycolic acid, lactic acid, etc.), hydroxy-dicarboxylic acids (e.g., malic acid, etc.), hydroxytricarboxylic acids (e.g., citric acid, etc.), etc. and which has a free carboxyl group; poly-α-cyanoacrylic acid esters; polyamino acids (e.g., poly-g-benzyl-L-glutamic acid, etc.); maleic anhydride copolymer (e.g., styrene-maleic acid copolymer, etc.), etc.

The copolymers may be any of random, block and graft copolymers. When the above α-hydroxycarboxylic acids, hydroxydicarboxylic acids and hydroxytricarboxylic acids have optical activity in their molecules, any one of D-isomers, L-isomers and DL-isomers may be used. Among others, α-hydroxycarboxylic acid polymer (preferably lactic acid-glycolic acid polymer), its ester, poly-α-cyanoacrylic acid esters, etc. are preferable, and lactic acid-glycolic acid polymer, and its ester are more preferable.

When the lactic acid-glycolic acid polymer is used as the biodegradable polymer, the molar ratio (mole %) ranges preferably from 100/0 to 40/60 and more preferably from 100/0 to 50/50.

In general, the weight-average molecular weight of the above lactic acid-glycolic acid polymer ranges from about 3,000 to about 50,000, preferably about 4,000 to about 40,000, and more preferably about 5,000 to about 30,000. Degree of dispersion (weight-average molecular weight/number-average molecular weight, hereinafter also referred to as dispersity) usually ranges from about 1.2 to about 4.0, preferably from about 1.5 to about 3.5.

In the present specification, the weight-average molecular weight, number-average molecular weight and dispersity mean molecular weights and dispersity determined by gel permeation chromatography (GPC) with 14 polymers of polystyrene as reference substances with weight-average molecular weights of 1,110,000, 707,000, 354,000, 189,000, 156,000, 98,900, 66,437, 37,200, 17,100, 9,830, 5,870, 2,500, 1,303 and 500, respectively. The determination was carried out using GPC column KF804L×2 (manufactured by Showa Denko K.K., Japan) and using chloroform as the mobile phase.

To calculate number-average molecular weight, the biodegradable polymer is dissolved in a mixed solvent of acetone and methanol and the solution is titrated with alcoholic potassium hydroxide solution using phenol-phthalein as an indicator to determine the terminal carboxyl group content. This value is hereinafter referred to as number-average molecular weight by end-group determination. While the number-average molecular weight by end-group determination is an absolute value, that by GPC determination is a relative value that varies depending on various analytical conditions (for example, the kind of mobile phase, the kind of column, reference substance, selection of slice width, selection of baseline, etc.). It is therefore difficult to have an absolute numerical representation of the latter. However, for example, in the case of a polymer having a terminal carboxyl group and produced from lactic acid and glycolic acid by catalyst-free polycondensation, the number-average molecular weight by GPC and the number-average molecular weight by end-group determination almost agree with each other. The description that the number-average molecular weight by GPC and end-group determination "almost agree" here denotes that the latter falls within the range from about 0.2 to about 1.5 times, preferably about 0.3 to about 1.2 times of the former.

The lactic acid-glycolic acid polymer can be produced by, for example, catalyst-free polycondensation from lactic acid and glycolic acid (Japanese Patent Unexamined Publication No. 28521/1986) or ring-opening polymerization with catalyst from cyclic lactide, glycolide, etc. (Encyclopedic Handbook of Biomaterials and Bioengineering Part A: Materials, Volume 2, Marcel Dekker, Inc. (1995)).

The polymer produced by ring-opening polymerization has little or no carboxyl group, however, a polymer having a terminal carboxyl group obtained by chemically treating the former polymer (J. Controlled Release, Vol. 41, pages 249-257 (1996)) can be used for the present invention.

The above-mentioned lactic acid-glycolic acid polymer having a terminal carboxyl group can be synthesized by general synthetic methods (e.g. catalyst-free polycondensation described in JP-A-28521/1986), without any problem. Moreover, the polymer having free carboxyl groups at unspecified positions can be synthesized by known methods (for example, WO94/15587).

As the lactic acid-glycolic acid polymer having a terminal carboxyl group, obtained by chemical treatment after ring-opening polymerization, that available from, for example, Boehringer Ingelheim KG can be employed.

Esters of the lactic acid-glycolic acid polymer can be produced by, for example, known methods from the lactic acid-glycolic acid polymer having a free carboxyl group (for example, Japanese Patent Unexamined Publication No. 278018/1995).

These biodegradable polymers can be used alone or in combination with two or more kinds of the polymers.

The polyvalent metal which may be incorporated into the sustained-release preparation of the present invention may be any metal, as long as it is a metal that does not adversely affect the living body. Examples of the metal include polyvalent metals such as a divalent metal (e.g., iron, zinc, copper, calcium, magnesium, aluminum, tin, manganese, etc.), a trivalent metal (e.g., iron, aluminum, manganese, etc.), a tetravalent metal (e.g., tin, etc.), etc.

In the sustained-release preparation of the present invention, these metals may be present in the form of a compound with an inorganic substance, a compound with an organic compound, a metal oxide [hereinafter, these three kinds of compounds are referred to as a polyvalent metal compound], etc.; in the form of a metal ion; or in a form of a complex with both of the compounds having angiotensin II antagonistic activity, its pro-drug or their salt, and the biodegradable polymer or either one of them.

Preferred examples of the polyvalent metal include iron, aluminum, zinc, calcium, magnesium, etc., and in particular, zinc is preferable. Among others, zinc derived from zinc oxide is preferable.

Examples of the inorganic substance include an inorganic acid, etc. such as hydrogen halogenide (e.g., hydrochloric acid, hydrobromic acid, hydroiodic acid, hydrofluoric acid, etc.), sulfuric acid, nitric acid, thiocyanic acid, etc.

Examples of the organic substance include an organic acid, etc. such as an aliphatic carboxylic acid, an aromatic acid, and acetylacetone, etc.

Preferred examples of the aliphatic carboxylic acid include a $C_{1-9}$ aliphatic carboxylic acid (e.g., aliphatic mono-, di- or tri-carboxylic acid, etc.), etc., and the aliphatic carboxylic acid may be saturated or unsaturated.

Examples of the aliphatic mono-carboxylic acid include a $C_{1-9}$ saturated aliphatic mono-carboxylic acid (e.g., carbonic acid, acetic acid, propionic acid, butyric acid, valeric acid, caproic acid, enanthic acid, caprylic acid, pelargonic acid, capric acid, etc.), a $C_{2-9}$ unsaturated aliphatic mono-carboxylic acid (e.g., acrylic acid, propiolic acid, methacrylic acid, crotonic acid, isocrotonic acid, etc.), etc.

Examples of the aliphatic di-carboxylic acid include a $C_{2-9}$ saturated aliphatic di-carboxylic acid (e.g., malonic acid, succinic acid, glutaric acid, adipic acid, pimelic acid, etc.), a $C_{2-9}$ unsaturated aliphatic di-carboxylic acid (e.g., maleic acid, fumaric acid, citraconic acid, mesaconic acid, etc.), etc.

Examples of the aliphatic tri-carboxylic acid include a $C_{2-9}$ saturated aliphatic tri-carboxylic acid (e.g., tricarballylic acid, 1,2,3-butanetricarboxylic acid, etc.), etc.

The above-mentioned aliphatic carboxylic acid may have 1-2 hydroxy groups, and examples of the aliphatic carboxylic acid having a hydroxy group include glycolic acid, lactic acid, glyceric acid, tartronic acid, malic acid, tartaric acid, citric acid, etc.

As the aliphatic carboxylic acid, an aliphatic mono-carboxylic acid is preferable, a $C_{2-9}$ aliphatic carboxylic acid is more preferable, and in particular, acetic acid is preferable.

Examples of the aromatic acid include benzoic acid, salicylic acid, phenolsulfonic acid, etc.

Examples of the polyvalent metal compound include a salt of an inorganic acid with iron [e.g., iron halogenide (e.g., iron chloride, iron bromide, iron iodide, iron fluoride, etc.), iron sulfate, iron nitrate, iron thiocyanate, etc.], a salt of an organic acid with iron [e.g., iron aliphatic carboxylate (e.g., iron carbonate, iron acetate, iron glycolate, iron lactate, iron tartarate, etc.), a salt of an aromatic acid with iron (e.g., iron benzoate, iron salicylate, iron phenolsulfonate, etc.)], iron acetylacetonate, etc.;

a salt of an inorganic acid with zinc [e.g., zinc halogenide (e.g., zinc chloride, zinc bromide, zinc iodide, zinc fluoride, etc.), zinc sulfate, zinc nitrate, zinc thiocyanate, etc.], a salt of an organic acid with zinc [e.g., zinc aliphatic carboxylate (e.g., zinc carbonate, zinc acetate, zinc glycolate, zinc lactate, zinc tartarate, etc.), a salt of an aromatic acid with zinc (e.g., zinc benzoate, zinc salicylate, zinc phenolsulfonate, etc.)], zinc acetylacetonate, etc.;

a salt of an inorganic acid with calcium [e.g., calcium halogenide (e.g., calcium chloride, calcium bromide, calcium iodide, calcium fluoride, etc.), calcium sulfate, calcium nitrate, calcium thiocyanate, etc.], a salt of an organic acid with calcium [e.g., calcium aliphatic carboxylate (e.g., calcium carbonate, calcium acetate, calcium propionate, calcium oxalate, calcium tartarate, calcium lactate, calcium citrate, calcium gluconate, etc.), a salt of an aromatic acid with calcium (e.g., calcium benzoate, calcium salicylate, etc.)], calcium acetylacetonate, etc.;

a salt of an inorganic acid with magnesium [e.g., magnesium halogenide (e.g., magnesium chloride, magnesium bromide, magnesium iodide, magnesium fluoride, etc.), magnesium sulfate, magnesium nitrate, magnesium thiocyanate, etc.], a salt of an organic acid with magnesium [e.g., magnesium aliphatic carboxylate (e.g., magnesium carbonate, magnesium acetate, magnesium propionate, magnesium oxalate, magnesium tartarate, magnesium lactate, magnesium citrate, magnesium gluconate, etc.), a salt of an aromatic acid with magnesium (e.g., magnesium benzoate, magnesium salicylate, etc.)], magnesium acetylacetonate, etc.; and metal oxide (e.g., iron oxide, zinc oxide, calcium oxide, magnesium oxide, aluminum oxide, copper oxide, manganese oxide, etc.), etc.

As the polyvalent metal compound, iron chloride, iron acetylacetonate, zinc acetate, zinc acetylacetonate, calcium acetate, calcium acetylacetonate, magnesium acetate, magnesium acetylacetonate, zinc oxide, etc. are preferable, and zinc oxide is more preferable.

In the present invention, all or a part of the polyvalent metal which may be incorporated into the sustained-release preparation of the present invention may be used in a form of a salt of the biodegradable polymer with one or more kinds of the polyvalent metals. Said salt of the biodegradable polymer with the polyvalent metal can be produced according to a method described in Japanese Patent Unexamined Publication No. 221420/1997 or a similar method thereto.

Examples of the preferred embodiments of the sustained-release preparation of the present invention include a sustained-release preparation comprising a compound having angiotensin II antagonistic activity, its pro-drug or their salt [hereinafter, these compounds are referred to as a compound having AII antagonistic activity], a biodegradable polymer and polyvalent metal, and examples of the production method of said preparation include a method for producing said sustained-release preparation, which comprises removing the solvent from a solution containing a compound having AII antagonistic activity, a biodegradable polymer and a polyvalent metal, etc.

The polyvalent metal may be incorporated into said solution by using, as a starting material, a complex of the polyvalent metal with both of the compounds having angiotensin II antagonistic activity, its pro-drug or their salt, and the biodegradable polymer or either one of them; by adding the polyvalent metal compound to said solution; etc. All or a part of the polyvalent metal compound added to said solution may form a complex with both of the compounds having AII antagonistic activity and the biodegradable polymer or either one of them in said solution.

In the sustained-release preparation of the present invention, the amount of the compound having AII antagonistic activity and a polyvalent metal compound varies depending on the kind of compound having AII antagonistic activity, desired pharmaceutical effect, duration for maintaining said effect, etc. For example, when the sustained-release preparation of the present invention consists of the compound having AII antagonistic activity and the biodegradable polymer, the amount of the compound having AII antagonistic activity is usually about 1 to about 50 weight %, preferably about 5 to about 45 weight %, more preferably about 10 to about 40 weight % relative to addition of said two components, the compound having AII antagonistic activity and the biodegradable polymer. When the sustained-release preparation of the present invention consists of the compound having AII antagonistic activity, the polyvalent metal compound and the biodegradable polymer, the amount of the compound having AII antagonistic activity is usually about 1 to about 50 weight %, preferably about 15 to 45 weight %, more preferably about 20 to 40 weight % relative to addition of said three components, and on the other hand, the amount of the polyvalent metal compound is usually about 0 to about 20 weight %, preferably about 2 to about 15 weight %, more preferably about 4 to about 10 weight %.

The sustained-release preparation of the present invention may be administered in any form and is preferably formulations for non-oral administration. Examples of said formulations include percutaneous formulations, indwellable formulations, injectable microcapsules, etc. Among them, injectable microcapsules are preferable, since they are long in duration for maintaining pharmaceutical effect and reduce the burden on the patient.

The production methods of the sustained-release preparation of the present invention, e.g. microcapsule (hereinafter also referred to as microsphere), which comprises a compound having AII antagonistic activity and a biodegradable polymer are exemplified as follows:

(I) in-water drying (i) O/W method

The compound having AII antagonistic activity and, in addition, the polyvalent metal compound when it is needed are added to an organic solvent solution of the biodegradable polymer at a ratio by weight as defined in the above-mentioned "amount of the compound having AII antagonistic activity and the polyvalent metal compound", to give an organic solvent solution of the biodegradable polymer containing the compound having AII antagonistic activity and, if necessary, the polyvalent metal compound. Either or both of the compounds having AII antagonistic activity and the polyvalent metal compound may not be dissolved in the organic solvent solution of the biodegradable polymer and may be dispersed in said solution. When either or both of the components is dispersed in said solution, it is preferable to finely disperses aid components according to a conventional method such as homogenization, ultrasonication, etc.

Examples of said organic solvent include halogenated hydrocarbons (e.g., dichloromethane, chloroform, dichloroethane, trichloroethane, carbon tetrachloride, etc.), ethers (e.g., ethylether, isopropylether, etc.), fatty acid esters (e.g., ethyl acetate, butyl acetate, etc.), aromatic hydrocarbons (e.g., benzene, toluene, xylene, etc.), alcohols (for example, ethanol, methanol, etc.), acetonitrile, etc. These solvents may be used singly or in combination.

Among others, as the halogenated hydrocarbon, dichloromethane is preferable and, as the alcohol, ethanol, methanol, etc. is preferable. These solvents may be used as a mixed solution at an appropriate ratio. A preferred example of the alcohol to be mixed with dichloromethane is ethanol when the compound having AII antagonistic activity contains a tetrazolyl group; and methanol when the compound having AII antagonistic activity contains a 4,5-dihydro-5-oxo-1,2,4-oxadiazol-3-yl group.

To the above-mentioned organic solvent solution, an additive may be added. Examples of the additives include solubilizer which maintains stability and solubility of the active ingredient such as carbonic acid, oxalic acid, citric acid, phosphoric acid, hydrochloric acid, sodium hydroxide, arginine, lysine and their salts, etc. Further, as stabilizers of the drug, there can be added, for example, albumin, gelatin, citric acid, sodium ethylenediaminetetraacetate, dextrin, sodium hydrogensulfite, polyols such as polyethyleneglycol, etc., etc., and as preservatives there can be added, for example, conventional para-oxybenzoic acid esters (e.g. methylparaben, propylparaben, etc.), benzylalcohol, chlorobutanol, thimerosal, etc.

The concentration of the biodegradable polymer in the organic solvent solution varies depending on the molecular weight of the biodegradable polymer and kind of the organic solvent. For example, when dichloromethane is used as an organic solvent, the concentration of the biodegradable polymer in the organic solvent solution is generally selected from the range of about 0.5 to about 70 weight %, more preferably about 1 to about 60 weight %, and in particular about 2 to about 50 weight %. Further, when ethanol or methanol and dichloromethane is used as a mixed organic solvent, the concentration of dichloromethane in the organic solvent solution is generally selected from the range of about 10 to about 99 volume %, more preferably about 20 to about 98 volume %, and in particular about 30 to about 95 volume %.

The thus obtained organic solvent solution of the biodegradable polymer, said solvent containing the compound having AII antagonistic activity and, in addition, polyvalent metal compound when it is needed is added to aqueous phase (or referred to as outer aqueous phase) to form O(oil phase)/W(aqueous phase) emulsion, followed by evaporation of the solvent in oil phase to yield microcapsules. The volume of the aqueous phase is generally selected from the range of about 1 to about 10,000 times the volume of the oil phase, more preferably about 5 to about 5,000 times, and in particular, about 10 to about 2,000 times.

Any emulsifier may be added to the above outer aqueous phase, as long as it can contribute to the formation of a stable O/W emulsion. Examples of the emulsifiers include anionic surfactants (sodium oleate, sodium stearate, sodium lauryl sulfate, etc.), non-ionic surfactants (polyoxy-ethylene-sorbitan fatty acid esters [Tween 80, Tween 60; Atlas Powder], polyoxyethylene-castor oil derivatives [HCO-60, HCO-50; Nikko Chemicals], etc.), polyvinylpyrrolidone, polyvinylalcohol, carboxymethylcellulose, lecithin, gelatin, hyaluronic acid, etc. These emulsifiers can be used independently or in combination. The concentration may be selected from about 0.01 to about 10 weight %, preferably about 0.05 to about 5 weight %.

To the outer aqueous phase, an osmotic pressure adjustor may be added. Any osmotic pressure adjustor can be employed so long as it produces osmotic pressure in an aqueous solution thereof.

Examples of the osmotic pressure adjustor include polyhydric alcohols, monovalent alcohols, monosaccharides, disaccharides, oligosaccharides, amino acids or their derivatives, etc.

Examples of the above polyhydric alcohols include dihydric alcohols such as glycerin, etc., pentahydric alcohols such as arabitol, xylitol, adonitol, etc., hexahydric alcohols such as mannitol, sorbitol, dulcitol, etc., etc. Among others, hexahydric alcohols are preferable and in particular, mannitol is preferable.

Examples of the above monovalent alcohols include methanol, ethanol, isopropyl alcohol, etc. Among others, methanol is preferable.

Examples of the above monosaccharides include pentoses such as arabinose, xylose, ribose, 2-deoxyribose, etc., hexoses such as glucose, fructose, galactose, mannose, sorbose, rhamnose, fucose, etc. Among others, hexoses are preferable.

Examples of the above oligosaccharides include trisaccharides such as maltotriose, raffinose, etc., tetrasaccharides such as stachyose, etc., etc. Among others, trisaccharides are preferable.

Examples of the derivatives of the above mentioned monosaccharides, disaccharides and oligosaccharides include glucosamine, galactosamine, glucuronic acid, galacturonic acid, etc.

Examples of the amino acids include any one of L-isomers and preferred examples include glycine, leucine, arginine, etc. Among others, L-arginine is preferable.

These osmotic pressure adjustors may be used alone or as a mixture of two or more of them.

These osmotic pressure adjustors are usually used at the concentration which makes the osmotic pressure of the outer aqueous phase about 1/50 to about 5 times, preferably about 1/25 to about 3 times of that of physiological saline.

To remove the organic solvent, per se known methods or methods analogous thereto are employed. For example, it is carried out by evaporating the organic solvent by stirring with a propeller-type stirrer, magnetic stirrer, etc. under atmospheric pressure or gradually reducing pressure or while controlling degree of vacuum by using a rotary evaporator, etc., etc.

The thus obtained microcapsules are collected by centrifugation or filtration. Then, the compound having AII antagonistic activity, carriers therefor, emulsifiers, etc. attached onto the surface of the microcapsules are washed with distilled water repeatedly several times, dispersed in distilled water, etc., and subjected to freeze-drying. In freeze drying, aggregation inhibitors may be added to avoid aggregation of the particles. Examples of said aggregation inhibitors include water-soluble polysaccharides such as mannitol, lactose, glucose, starch (e.g., corn starch, etc.), etc., amino acid such as glycine, etc., protein such as fibrin, collagen, etc., etc. Among others, mannitol is preferable.

After freeze drying, further removal of water and an organic solvent may be carried out by warming the microcapsules under reduced pressure and under the conditions where the microcapsules do not attach to each other, if desired. Preferably, the microcapsules are warmed at an appropriate temperature which is a little bit higher than median glass transition temperature (determined using differential scanning calorimeter at temperature increments of 10 or 20° C. per minute) of the biodegradable polymer. More preferably, the microcapsules are warmed at temperatures ranging from median glass transition temperature to about 3° C. higher than median glass transition temperature of the biodegradable polymer. In particular, when lactic acid-glycolic acid polymer is used as the biodegradable polymer, the microcapsules are preferably warmed at temperatures ranging from median glass transition temperature to about 10° C. higher than median glass transition temperature of the polymer, more preferably from median glass transition temperature to about 5° C. higher than median glass transition temperature of the polymer.

Warming time varies depending on the amount of the microcapsules to be treated, etc. In general, about 12 hours to about 168 hours, preferably about 24 hours to about 120 hours, and in particular, about 48 hours to about 96 hours after the temperature of the microcapsules themselves reach the desired temperature are preferable.

A method for warming the microcapsules is not limited to a specific method, and any method can be employed as long as a set of the microcapsule are uniformly warmed.

Examples of the method for warming and drying the microcapsules include that in constant temperature bath, fluidized bath, moving bath or kiln, that by micro wave, etc. Among others, the method for warming and drying the microcapsules in constant temperature bath is preferable.

(ii) W/O/W Method

The compound having AII antagonistic activity is dissolved in water, and if necessary a carrier therefor such as a polyvalent metal compound (e.g. zinc acetate), basic amino acid (for example, arginine, histidine, lysine), gelatin, agar, polyvinylalcohol, etc. is added to the solution, to give an inner aqueous phase.

The concentration of the drug in the inner aqueous phase is generally selected from the range of about 0.1-80 weight %, more preferably about 1-70 weight %, and in particular about 2-60 weight %.

To the inner aqueous phase, as pH regulators to maintain the stability and solubility of the drug, carbonic acid, oxalic acid, citric acid, phosphoric acid, hydrochloric acid, sodium hydroxide, arginine, lysine and their salts, etc. may be added. Further, as stabilizers of the drug, there can be added, for example, albumin, gelatin, citric acid, sodium ethylenediaminetetraacetate, dextrin, sodium hydrogensulfite, polyols such as polyethyleneglycol, etc., etc., and as preservatives there can be added, for example, conventional paraoxybenzoic acid esters (e.g. methylparaben, propylparaben, etc.), benzylalcohol, chlorobutanol, thimerosal, etc.

The thus obtained inner aqueous phase is added to an organic solvent solution of the biodegradable polymer (oil phase) optionally containing the polyvalent metal compound, and the mixture is emulsified with known methods using a homogenizer, ultrasonicator, etc. to form W/O emulsion.

Examples of the organic solvent include halogenated hydrocarbon (e.g., dichloromethane, chloroform, dichloroethane, trichloroethane, carbon tetrachloride, etc.), ethers (e.g., ethylether, isopropylether, etc.), fatty acid esters (e.g., ethyl acetate, butyl acetate, etc.), aromatic hydrocarbon (e.g., benzene, toluene, xylene, etc.), alcohols (for example, ethanol, methanol, etc.), acetonitrile, etc. These solvents may be used as a solution mixed at an appropriate ratio.

Among others, halogenated hydrocarbons are preferable, and in particular dichloromethane is preferable.

The concentration of the biodegradable polymer in the organic solvent solution varies depending on the molecular weight of the biodegradable polymer and kind of the organic solvent. For example, when dichloromethane is used as an organic solvent, the concentration of the biodegradable polymer in the organic solvent solution is generally selected from the range of about 0.5 to about 70 weight %, preferably about 1 to about 60 weight %, more preferably about 2 to about 50 weight %.

The thus obtained W/O emulsion containing the compound having AII antagonistic activity, the biodegradable polymer and, if necessary, the polyvalent metal compound is added to an aqueous phase (outer aqueous phase) to give W(inner aqueous phase)/O(oil phase)/W(outer aqueous phase) emulsion, from which the solvent in the oil phase is evaporated to give microcapsules. The volume of the outer aqueous phase is generally selected from the range of about 1 to about 10,000 times the volume of the oil phase, more preferably about 5 to about 5,000 times, and in particular, about 10 to about 2,000 times.

Examples of the emulsifiers and osmotic pressure adjustors which may be added to the above-mentioned outer aqueous phase, and the preparation methods after addition of these additives are similar to those described in the above item (I)(i).

(II) Phase Separation

In producing microcapsules by the phase separation method, an coacervating agent is gradually added to the above-mentioned organic solvent solution of the biodegradable polymer containing the compound having AII antagonistic activity and, in addition, the polyvalent metal compound when it is needed as described in the above item (I), in-water drying, during stirring to precipitate and solidify the microcapsules. The volume of the coacervating agent is generally selected from the range of about 0.01 to about 1,000 times the volume of the oil phase, more preferably about 0.05 to about 500 times, and in particular, about 0.1 to about 200 times.

Any coacervating agent is acceptable, as long as it is a polymer, mineral oil, vegetable oil, etc. that is miscible in the organic solvent and does not dissolve both of the compound having AII antagonistic activity and the biodegradable polymer. For example, silicon oil, sesame oil, soybean oil, corn oil, cotton seed oil, coconut oil, linseed oil, mineral oil, n-hexane, n-heptane, etc. are employed. These may be used in combination.

The thus obtained microcapsules are separated, repeatedly washed with heptane, etc. to remove the coacervating agent, other than the compound having AII antagonistic activity and the biodegradable polymer, and then dried under reduced pressure. Alternatively, the microcapsules are washed with the methods similar to those described in the above item (I)(i), in-water drying, subjected to freeze-drying, and then warmed and dried.

(III) Spray Drying

In producing microcapsules by this method, the above-mentioned organic solvent solution of the biodegradable polymer containing the compound having AII antagonistic activity and optionally containing the polyvalent metal compound as described in the above item (I), in-water drying, is sprayed via a nozzle into the drying chamber of a spray drier to volatilize the organic solvent in the fine droplets in a very short time to yield the microcapsules. Examples of the nozzles include double-fluid nozzle, pressure nozzle, rotary disc nozzle, etc. Thereafter, if necessary, the microcapsules are washed with the methods similar to those described in the above item (I), in-water drying, subjected to freeze-drying, and then warmed and dried.

In addition to the above-described dosage form of the microcapsules, the organic solvent solution of the biodegradable polymer containing the compound having AII antagonistic activity and, in addition, the polyvalent metal compound when it is needed as described in the item (I), in-water drying, may be subjected to evaporation of the organic solvent and water while controlling the degree of vacuum by using a rotary evaporator, etc., and the residue may be crushed with jet mill, etc. to yield fine powders.

The thus obtained fine powders may be washed with the methods similar to those described in the above item (I), in-water drying, subjected to freeze-drying, and then warmed and dried.

The release of the compound having AII antagonistic activity from the thus obtained microcapsules or fine powders can be controlled by the degradation rate of the employed biodegradable polymer and kind and/or amount of the added polyvalent metal compound.

The sustained-release preparation of the present invention can be used for the production of various preparations, as it is or as a raw material and administered as injections or implants intramuscularly, subcutaneously, into organs, etc.; as transmucosal preparations into the nasal cavity, rectum, uterus, etc.; oral preparations (e.g., capsules (e.g., hard capsules, soft capsules, etc.), solid preparations such as granules, powders, etc., liquid preparations such as syrups, emulsions, suspensions, etc., etc.); etc. Also, the sustained-release preparation of the present invention can be administered using needleless injectors.

For example, when the sustained-release preparation according to the present invention is to be processed into injections, it is dispersed together with a dispersing agent (e.g., surfactants such as Tween 80, HCO-60, etc., polysaccharides such as sodium hyaluronate, carboxymethylcellulose, sodium alginate, etc., etc.), a preservative (e.g., methylparaben, propylparaben, etc.), an isotonizing agent (e.g., sodium chloride, mannitol, sorbitol, glucose, proline, etc.), etc. to form an aqueous suspension, or it is dispersed together with vegetable oil such as sesame oil, corn oil, etc. to form an oily suspension, said suspensions being actually used as sustained-release injections.

Particle size of the sustained-release preparation of the present invention is selected from the range satisfying the dispersibility and needle-passability requirements when it is used as suspension. For example, the average diameter ranges from about 0.1 to about 300 μm, preferably from about 0.5 to about 150 μm, more preferably from about 1 to about 100 μm.

In order to prepare a sterile preparation of the sustained-release preparation of the present invention, a method for sterilizing all production steps, a method for sterilizing with γ-rays, a method for adding a preservative, etc. are employed, and there is no limitation to a specific method.

With low toxicity, the sustained-release preparation of the present invention can be used in mammals (e.g., human, bovine, swine, dog, cat, mouse, rat, rabbit, etc.) as a safe medicine, etc.

Varying depending on type, content and dosage form of the compound having AII antagonistic activity as the active ingredient; duration of release of the compound having AII antagonistic activity; target disease; subject animal; etc., the dose of the sustained-release preparation of the present invention is within the range of an effective amount of the compound having AII antagonistic activity. For example, the dose per administration of the active ingredient, the compound having AII antagonistic activity, is preferably chosen within the range from about 0.01 mg to about 10 mg/kg body weight per adult, more preferably from about 0.05 mg to about 5 mg/kg body weight per adult, when the sustained-release preparation is a 1-month preparation. The dose per administration of the sustained-release preparation of the present invention is preferably chosen within the range from about 0.05 mg to about 50 mg/kg body weight per adult, more preferably from about 0.1 mg to about 30 mg/kg body weight per adult.

Number of administrations can be appropriately selected from once per a few weeks, once per a month, or once per a few months (e.g., 3 months, 4 months, 6 months, etc.), etc., depending on type, content and dosage form of the active ingredient, the compound having AII antagonistic activity, duration of release of the compound having AII antagonistic activity, target diseases, subject animals, etc.

The compound having AII antagonistic activity possesses high safety and therefore increase of concentration of said compound in blood just after administration of the sustained-release injection does not cause excess reduction of blood pressure. Thus, the sustained-release preparation of the present invention can be used for the diseases described below and can maintain constant concentration of the drug in blood during day and night. Therefore, the dose and numbers of administration can be reduced, compared with administration of conventional oral preparations. Moreover, the change of concentration of the drug in blood is not remarkable and condition of the patient does not change due to interruption in taking the drug, etc. Therefore, it is expected that the treatment effect of the drug will become clearer by administration of the sustained-release preparation of the present invention.

Examples of the diseases include circulatory disease, etc. such as hypertension, cardiac disease (hypercardia, cardiac insufficiency, myocardial infarction, etc.), nephritis, cerebral apoplexy, etc., which are caused by vasoconstriction expressed via angiotensin II receptors.

The sustained-release preparation of the present invention is useful for the prevention or treatment of hypertension, hypercardia, cardiac insufficiency, myocardial infarction, cerebral apoplexy, ischemic peripheral circulation disturbances, myocardial ischemia, vein insufficiency, progressive cardiac insufficiency after myocardial infarction, diabetic complication, diabetic retinopathy, diabetic nephropathy, nephritis, glomerulonephritis, arteriosclerosis, angiohypertrophy, vascular hypertrophy or obstruction after intervention (e.g. percutaneous transluminal coronary angioplasty, etc.), vascular reobstruction after bypass surgery, hyperaldosteronism, glomerulosclerosis, renal insufficiency, glaucoma, intraocular high tension, hyperlipemia, angina pectoris, aneurysm, coronary arteriosclerosis, cerebral arteriosclerosis, peripheral arteriosclerosis, thrombosis, disease of central nervous system, Alzheimer's disease, deficiency of memory, depression, amnesia, senile dementia, sensory disturbances, multiple system organ failure, a disease due to endothelial dysfunction or scleroderma; or for the prevention or amelioration of anxiety neurosis, catatonia, indisposition or dyspeptic symptoms.

As the method for the treatment of patients, it is considered to administer to a patient conventional oral preparations containing a compound having AII antagonistic activity for a certain period to check the reaction of said patient and then to administer the sustained-release preparation of the present invention to the patient. The angiotensin II antagonist to be orally administered and that to be contained in the sustained-release preparation may be same or different. In addition, anti-hypertensive agent (e.g. calcium antagonist, diuretic, 1-blocker, etc.) other than angiotensin II antagonist may be previously administered to a patient to check the reaction of said patient and then the sustained-release preparation of the present invention may be administered to the patient. Moreover, the present sustained-release preparation may be used in combination with diuretic (oral preparation) which is usually used in combination with angiotensin II antagonist.

BEST MODE FOR CARRYING OUT THE INVENTION

The present invention is hereinafter described in more detail by means of the following Working Examples and Experimental Examples, which are not to be construed as limitative.

WORKING EXAMPLE 1

In a mixed solution of dichloromethane 3.5 ml and methanol 1.5 ml were dissolved 2-ethoxy-1-[[2'-(4,5-dihydro-5-oxo-1,2,4-oxadiazol-3-yl)biphenyl-4-yl]methyl]benzimidazole-7-carboxylic acid (hereinbelow, referred to as Compound A) 0.25 g and lactic acid-glycolic acid copolymer (lactic acid/glycolic acid: 75/25 (mole %); weight-average molecular weight: 10,700; number-average molecular weight: 6,100; number-average molecular weight by end-group determination: 3,770; Wako Pure Chemical) 2.25 g, and the solution was injected to 0.1 weight % polyvinylalcohol solution 500 ml, previously adjusted to 18° C., followed by stirring in a turbine homomixer at 7,000 rpm to yield O/W emulsion. The O/W emulsion was stirred at room temperature for 3 hours to volatilize dichloromethane and methanol and solidify the oil phase, which was then collected via centrifugation at 2,000 rpm.

The precipitate was again dispersed in distilled water, centrifuged and washed to remove the free drug, etc. After the collected microcapsules were re-dispersed in a small amount of distilled water, the dispersion was subjected to freeze-drying to give powdery microcapsules.

Yield of the microcapsules was 69%, entrapment ratio of Compound A in the microcapsules was 92%, and the content of Compound A in the microcapsules was 9.2%.

WORKING EXAMPLE 2

Disodium salt of Compound A 0.25 g was dissolved in distilled water 0.4 ml, and the solution was mixed with a solution of lactic acid-glycolic acid copolymer (the same as described in Working Example 1) 2.25 g in dichloromethane 4 ml. The mixture was stirred with a homogenizer to form W/O emulsion. The W/O emulsion was injected to 0.1 weight % polyvinylalcohol solution 500 ml, previously adjusted to 18° C., followed by stirring in a turbine homomixer at 7,000 rpm to yield W/O/W emulsion. The W/O/W emulsion was stirred at room temperature for 3 hours to volatilize dichloromethane and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water, the dispersion was subjected to freeze-drying to give powdery microcapsules.

Yield of the microcapsules was 50%, entrapment ratio of Compound A in the microcapsules was 37%, and the content of Compound A in the microcapsules was 3.7%.

WORKING EXAMPLE 3

In a mixed solution of dichloromethane 3.5 ml and methanol 2.5 ml were dissolved Compound A 0.4 g and lactic acid polymer ethyl ester (a biodegradable polymer, wherein a terminal carboxyl group of lactic acid polymer is esterified with ethyl; weight-average molecular weight: 10,200; number-average molecular weight: 5,680; Wako Pure Chemical) 1.6 g, and the solution was injected to 0.1 weight % polyvinylalcohol solution 800 ml containing 5% mannitol, previously adjusted to 18° C., followed by stirring in a turbine homomixer at 7,000 rpm to yield O/W emulsion. The O/W emulsion was stirred at room temperature for 3 hours to volatilize dichloromethane and methanol and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water, the dispersion was subjected to freeze-drying to give powdery microcapsules.

Yield of the microcapsules was 83%, entrapment ratio of Compound A in the microcapsules was 86%, and the content of Compound A in the microcapsules was 17.1%.

EXPERIMENTAL EXAMPLE 1

The microcapsule about 35 mg of which was obtained in Working Example 3 was dispersed in a solvent 0.3 ml (distilled water in which carboxymethylcellulose 0.25 mg, polysorbate 80 0.5 mg and mannitol 25 mg were dissolved), and the mixture was subcutaneously administered to the back of 7-week old male SD rats using 22G needles. At regular intervals after administration, blood was collected from the rats aorta abdominalis, and the rats were sacrificed to collect the microcapsules remaining at the administration site.

The amount of Compound A in the microcapsules was determined, and the results are shown in Table 1. In addition, the concentration of Compound A in blood was determined, and the results are shown in Table 2.

TABLE 1

|  | 1 day | 1 week | 2 weeks | 3 weeks | 4 weeks |
|---|---|---|---|---|---|
| W. Ex. 3 | 66% | 42% | 27% | 17% | 15% |

TABLE 2

|  | 1 day | 1 week | 2 weeks | 3 weeks | 4 weeks |
|---|---|---|---|---|---|
| W. Ex. 3 | 4.4 | 0.6 | 0.3 | 0.2 | 0.1 |
|  |  |  |  |  | (unit; μg/ml) |

WORKING EXAMPLE 4

To a solution of lactic acid-glycolic acid copolymer (lactic acid/glycolic acid: 75/25 (mole %); weight-average molecular weight: 14,000; number-average molecular weight: 4,200; number-average molecular weight by end-group determination: 4,090; Wako Pure Chemical) 2.4 g dissolved in dichloromethane 4.5 ml and ethanol 1 ml were added 2-ethoxy-1-[[2'-(1H-tetrazol-5-yl)biphenyl-4-yl]methyl]benzimidazole-7-carboxylic acid (hereinbelow, referred to as Compound B) 0.6 g and zinc oxide 0.09 g (particle size: 0.02 μm), and the mixture was shaken and stirred for 12 hours at room temperature to give a slightly turbid suspension. The suspension was injected to 0.1 weight % polyvinylalcohol solution 400 ml, previously adjusted to 15° C., followed by stirring in a turbine homomixer at 7,000 rpm to yield O/W emulsion. The O/W emulsion was stirred at room temperature for 3 hours to volatilize dichloromethane and ethanol and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water in which mannitol was dissolved, the dispersion was subjected to freeze-drying to give powdery microcapsules.

Entrapment ratio of Compound B in the microcapsules was 97%, and the content of Compound B in the microcapsules was 18.8%.

WORKING EXAMPLE 5

The amount of zinc oxide was changed to 0.057 g, and the microcapsules were produced according to a method similar to that described in Working Example 1. Entrapment ratio of Compound B in the microcapsules was 97%, and the content of Compound B in the microcapsules was 19.0%.

WORKING EXAMPLE 6

The amount of Compound B, zinc oxide and lactic acid-glycolic acid copolymer was changed to 0.9 g, 2.1 g and 0.12 g, respectively, and the microcapsules were produced according to a method similar to that described in Working Example 1.

Entrapment ratio of Compound B in the microcapsules was 96%, and the content of Compound B in the microcapsules was 27.8%.

WORKING EXAMPLE 7

The amount of zinc oxide was changed to 0.18 g, and the microcapsules were produced according to a method similar to that described in Working Example 3.

Entrapment ratio of Compound B in the microcapsules was 92%, and the content of Compound B in the microcapsules was 26.2%.

WORKING EXAMPLE 8

To a solution of lactic acid-glycolic acid copolymer (lactic acid/glycolic acid: 75/25 (mole %); weight-average molecular weight: 14,000; number-average molecular weight: 4,200; number-average molecular weight by end-group determination: 4,090; Wako Pure Chemical) 4.2 g dissolved in dichloromethane 9 ml and ethanol 1.5 ml were added Compound B 1.8 g and zinc oxide 0.3 g (particle size: 0.02 μm), and the mixture was shaken and stirred for 12 hours at room temperature to give a slightly turbid suspension. The suspension was injected to 0.1 weight % polyvinylalcohol solution 800 ml, previously adjusted to 15° C., followed by stirring in a turbine homomixer at 7,000 rpm to yield O/W emulsion. The O/W emulsion was stirred at room temperature for 3 hours to volatilize dichloromethane and ethanol and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water in which mannitol was dissolved, the dispersion was subjected to freeze-drying to give powdery microcapsules.

Entrapment ratio of Compound B in the microcapsules was 94%, and the content of Compound B in the microcapsules was 26.8%.

WORKING EXAMPLE 9

To a solution of lactic acid-glycolic acid copolymer (lactic acid/glycolic acid: 75/25 (mole %); weight-average molecular weight: 14,000; number-average molecular weight: 4,200; number-average molecular weight by end-group determination: 4,090; Wako Pure Chemical) 0.7 g dissolved in dichloromethane 1.5 ml and methanol 1 ml were added Compound A 0.3 g and zinc oxide 0.05 g (particle size: 0.02 μm), and the mixture was shaken and stirred for 12 hours at room temperature to give a slightly turbid suspension.

The suspension was injected to 0.1 weight % polyvinylalcohol solution 300 ml, previously adjusted to 15° C., followed by stirring in a turbine homomixer at 6,500 rpm to yield O/W emulsion. The O/W emulsion was stirred at room temperature for 3 hours to volatilize dichloromethane and methanol and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water in which mannitol was dissolved, the dispersion was subjected to freeze-drying to give powdery microcapsules.

Entrapment ratio of Compound A in the microcapsules was 91%, and the content of Compound A in the microcapsules was 25.9%.

WORKING EXAMPLE 10

To a solution of lactic acid-glycolic acid copolymer (lactic acid/glycolic acid: 75/25 (mole %); weight-average molecular weight: 14,000; number-average molecular weight: 4,200; number-average molecular weight by end-group determination: 4,090; Wako Pure Chemical) 1.8 g dissolved in dichloromethane 5 ml were added Compound B 1 g and zinc oxide 0.18 g (particle size: 0.02 μm), and the mixture was emulsified for 60 seconds with a small homogenizer to give a suspension. The suspension was injected to 0.1 weight % polyvinylalcohol solution 400 ml, previously adjusted to 15° C., followed by stirring in a turbine homomixer at 8,000 rpm to yield O/W emulsion. The O/W emulsion was stirred at room temperature for 3 hours to volatilize dichloromethane and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water in which mannitol was dissolved, the dispersion was subjected to freeze-drying to give powdery microcapsules.

Entrapment ratio of Compound B in the microcapsules was 96%, and the content of Compound B in the microcapsules was 32.0%.

WORKING EXAMPLE 11

Except that ethanol 0.8 ml was added to dichloromethane and for the slightly turbid suspension given by shaking and stirring for 12 hours at room temperature, the microcapsules were produced according to a method similar to that described in Working Example 7.

Entrapment ratio of Compound B in the microcapsules was 95%, and the content of Compound B in the microcapsules was 32.0%.

WORKING EXAMPLE 12

In a mixed solution of dichloromethane 4.5 ml and ethanol 0.7 ml were dissolved 1-(cyclohexyloxycarbonyloxy)ethyl 2-ethoxy-1-[[2'-(1H-tetrazol-5-yl)biphenyl-4-yl]methyl]benzimidazole-7-carboxylate (hereinbelow, referred to as Compound C) 0.9 g and lactic acid-glycolic acid copolymer (lactic acid/glycolic acid: 75/25 (mole %); weight-average molecular weight: 14,000; number-average molecular weight: 4,200; number-average molecular weight by end-group determination: 4,090; Wako Pure Chemical) 2.1 g, and to the solution was added zinc oxide 0.15 g (particle size: 0.02 μm). The mixture was shaken and stirred for 12 hours at room temperature to give a slightly turbid suspension. The suspension was injected to 0.1 weight % polyvinylalcohol solution 400 ml, previously adjusted to 15° C., followed by stirring in a turbine homomixer at 7,500 rpm to yield O/W emulsion. The OW emulsion was stirred at room temperature for 3 hours to volatilize dichloromethane and ethanol and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water in which mannitol was dissolved, the dispersion was subjected to freeze-drying to give powdery microcapsules.

Entrapment ratio of Compound C in the microcapsules was 96%, and the content of Compound C in the microcapsules was 27.4%.

WORKING EXAMPLE 13

Except that zinc oxide was not added, the microcapsules were produced according to a method similar to that described in Working Example 12.

Entrapment ratio of Compound C in the microcapsules was 98%, and the content of Compound C in the microcapsules was 30.0%.

WORKING EXAMPLE 14

In dichloromethane 5 ml were dissolved Compound C 1.2 g and lactic acid-glycolic acid copolymer (lactic acid/glycolic acid: 75/25 (mole %); weight-average molecular weight: 14,000; number-average molecular weight: 4,200; number-average molecular weight by end-group determination: 4,090; Wako Pure Chemical) 1.8 g, and to the solution was added zinc oxide 0.18 g (particle size: 0.02 μm). The mixture was shaken and stirred for 1 hour at room temperature to give a slightly turbid suspension. The suspension was injected to 0.1 weight % polyvinylalcohol solution 400 ml, previously adjusted to 15° C., followed by stirring in a turbine homomixer at 8,000 rpm to yield O/W emulsion. The O/W emulsion was stirred at room temperature for 3 hours to volatilize dichloromethane and ethanol and solidify the oil phase, which was then collected via centrifugation at 2,000 rpm. The precipitate was again dispersed in distilled water, centrifuged and washed to remove the free drug, etc. After the collected microcapsules were re-dispersed in a small amount of distilled water in which mannitol was dissolved, the dispersion was subjected to freeze-drying to give powdery microcapsules.

Entrapment ratio of Compound C in the microcapsules was 95%, and the content of Compound C in the microcapsules was 35.9%.

WORKING EXAMPLE 15

Except that zinc oxide was not added, the microcapsules were produced according to a method similar to that described in Working Example 4.

Entrapment ratio of Compound B in the microcapsules was 99%, and the content of Compound B in the microcapsules was 19.8%.

WORKING EXAMPLE 16

Except that zinc oxide was not added, the microcapsules were produced according to a method similar to that described in Working Example 9.

Entrapment ratio of Compound A in the microcapsules was 95%, and the content of Compound A in the microcapsules was 28.4%.

EXPERIMENTAL EXAMPLE 2

The microcapsule 25 mg obtained in Working Examples 4-14 was dispersed in 0.2 ml of a dispersant (distilled water 1 ml in which 5 mg of sodium carboxymethylcellulose, 1 mg of polysorbate 80 and 50 mg of mannitol were dissolved), and the mixture was subcutaneously administered to the back of the neck of 7-week old male SD rats using 22G needles. At regular intervals after administration, the rats were sacrificed by abdominal exsanguination and the microcapsules remaining at the administration site were collected.

The amount of the compound having AII antagonistic activity in the microcapsules was determined, and the results are shown in Table 3. In addition, the concentration of Compound B in blood when the microcapsules of Working Examples 4, 6 and 8 were administered is shown in Table 4.

TABLE 3

Average ratio of the compound having AII antagonistic activity remaining after subcutaneous administration of the microcapsules (n = 3 –5)

|  | 1 day | 1 week | 2 weeks | 3 weeks | 4 weeks |
| --- | --- | --- | --- | --- | --- |
| W. Ex. 4 | 90% | 62% | 36% | 11% | 3% |
| W. Ex. 5 | 85% | 60% | 18% | ND | ND |
| W. Ex. 6 | 88% | 63% | 33% | 11% | 3% |
| W. Ex. 7 | 94% | 78% | 55% | 43% | 26% |
| W. Ex. 8 | 86% | 62% | 38% | 18% | 7% |
| W. Ex. 9 | 87% | 58% | 21% | 1% | ND |
| W. Ex. 10 | 90% | 79% | 43% | 17% | 3% |
| W. Ex. 11 | 96% | 82% | 49% | 27% | 12% |
| W. Ex. 12 | 95% | 64% | 24% | 7% | ND |
| W. Ex. 13 | 76% | 29% | ND | ND | ND |
| W. Ex. 14 | 94% | 68% | 16% | 2% | MD |

ND: not done

TABLE 4

Average concentration of Compound B in blood after subcutaneous administration of the microcapsules (n = 5)

|  | 1 day | 1 week | 2 weeks | 3 weeks | 4 weeks |
| --- | --- | --- | --- | --- | --- |
| W. Ex. 4 | 125 ng/ml | 92 ng/ml | 126 ng/ml | 90 ng/ml | 32 ng/ml |
| W. Ex. 6 | 335 ng/ml | 247 ng/ml | 351 ng/ml | 169 ng/ml | 95 ng/ml |
| W. Ex. 8 | 134 ng/ml | 158 ng/ml | 166 ng/ml | 168 ng/ml | 101 ng/ml |

EXPERIMENTAL EXAMPLE 3

The microcapsule 2.5 mg obtained in Working Example 8 was dispersed in 0.2 ml of a dispersant (distilled water 1 ml in which 5 mg of sodium carboxymethylcellulose, 1 mg of polysorbate 80 and 50 mg of mannitol were dissolved), and the mixture was subcutaneously administered to the back of the neck of 28-week old male 12008SHR rats in which a blood pressure transmitter for telemetry was implanted, using 22G needles. After administration, blood pressure was monitored. The same preparation was subcutaneously administered to the back of the neck of 29-week old male 12008SHR rats. At regular intervals after administration, blood was collected from the tail vein. The concentration of Compound B in blood and hypotensive action of Compound B are shown in Table 5.

TABLE 5

Average concentration of Compound B in blood and hypotensive action after subcutaneous administration of the microcapsules (n = 3)

|  | 1 day | 1 week | 2 weeks | 3 weeks | 4 weeks |
| --- | --- | --- | --- | --- | --- |
| concentration (ng/ml) | 41 | 27 | 27 | 55 | 45 |
| hypotensive action (mmHg) | −21.4 | −14.4 | −17.4 | −22.7 | −20.9 |

INDUSTRIAL APPLICABILITY

The sustained-release preparation of the present invention contains a high amount of the compound having AII antagonistic activity and can control the release rate of the drug. Therefore, it shows angiotensin II antagonistic activity while maintaining circadian rhythm of blood pressure for a long time.

In addition, the sustained-release preparation of the present invention can maintain constant concentration of the drug in blood during day and night. Therefore, compared with administration of conventional oral preparations, the change of concentration of the drug in blood is not remarkable and the condition of the patient does not change due to change in administration time, interruption in taking the drug, intentional avoidance of taking the drug in the patients having few subjective symptoms, etc. Accordingly, it is expected that the treatment effect of the drug on circulatory disease, etc. such as hypertension, cardiac disease (hypercardia, cardiac insufficiency, myocardial infarction, etc.), nephritis, cerebral apoplexy, etc. will become clearer by administration of the sustained-release preparation of the present invention.

The invention claimed is:

1. An injectable sustained-release preparation which comprises a compound having angiotensin II antagonistic activity, its pro-drug or its salt, and a biodegradable polymer, wherein said compound having angiotensin II antagonistic activity is a compound selected from the group consisting of 2-ethoxy-1-[[2'-(1H-tetrazol-5-yl)biphenyl-4-yl]methyl]benzimidazole-7-carboxylic acid, 1-(cyclohexyloxycarbonyloxy)ethyl 2-ethoxy-1-[[2'-(1H-tetrazol-5-yl)biphenyl-4-yl]methyl]benzimidazole-7-carboxylate and 2-ethoxy-1-[[2'-(4,5-dihydro-5-oxo-1,2,4-oxadiazol-3-yl)biphenyl-4-yl]methyl]benzimidazole-7-carboxylic acid, and is formulated as an injectable sustained release preparation.

2. A sustained-release preparation according to claim 1, wherein the compound having angiotensin II antagonistic activity is 2-ethoxy-1-[[2'-(1H-tetrazol-5-yl)biphenyl-4-yl]methyl]benzimidazole-7-carboxylic acid or a salt thereof.

3. A sustained-release preparation according to claim 1, wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate or a salt thereof.

4. A sustained-release preparation according to claim 1, wherein the compound having angiotensin II antagonistic activity is 2-ethoxy-1-[[2'-(4,5-dihydro-5-oxo-1,2,4-oxadiazol-3-yl)biphenyl-4-yl]methyl]benzimidazole-7-carboxylic acid or a salt thereof.

5. A sustained-release preparation according to claim 1, wherein the biodegradable polymer is α-hydroxycarboxylic acid polymer.

6. A sustained-release preparation according to claim 5, wherein the α-hydroxycarboxylic acid polymer is lactic acid-glycolic acid polymer.

7. A sustained-release preparation according to claim 6, wherein the molar ratio of lactic acid and glycolic acid is 100/0-40/60.

8. A sustained-release preparation according to claim 5, wherein the weight-average molecular weight of the polymer is 3,000-50,000.

9. A sustained-release preparation according to claim 1, which further comprises a polyvalent metal.

10. A sustained-release preparation according to claim 9, wherein the polyvalent metal is zinc.

11. An injectable sustained-release preparation which comprises a compound having angiotensin II antagonistic activity, its pro-drug or its salt, a biodegradable polymer and a polyvalent metal, wherein said compound having angiotensin II antagonistic activity is a compound selected from the group consisting of 2-ethoxy-1-[[2'-(1H-tetrazol-5-yl)biphenyl-4-yl]methyl]benzimidazole-7-carboxylic acid, 1-(cyclohexyloxycarbonyloxy)ethyl 2-ethoxy-1-[[2'-(1H-tetrazol-5-yl)biphenyl-4-yl]methyl]benzimidazole-7-carboxylate and 2-ethoxy-1-[[2'-(4,5-dihydro-5-oxo-1,2,4-oxadiazol-3-yl)biphenyl-4-yl]methyl]benzimidazole-7-carboxylic acid, and is formulated as a sustained release preparation for injection.

12. A method for producing the sustained-release preparation as claimed in claim 1, which comprises removing the solvent from a solution containing a compound having angiotensin II antagonistic activity, its pro-drug or their salt, and a biodegradable polymer.

13. A method for producing a sustained-release preparation as claimed in claim 11, which comprises removing the solvent from a solution containing a compound having angiotensin II antagonistic activity, its pro-drug or their salt, a biodegradable polymer and a polyvalent metal.

14. A method according to claim 13, wherein the polyvalent metal is zinc.

15. A pharmaceutical composition comprising the sustained-release preparation as claimed in claim 1.

16. A composition as claimed in claim 15, which is for the prevention or treatment of circulatory disease.

17. A composition as claimed in claim 15, which is for the prevention or treatment of hypertension.

18. A composition as claimed in claim 15, which is for the prevention or treatment of hypercardia, cardiac insufficiency, myocardial infarction, cerebral apoplexy, ischemic peripheral circulation disturbances, myocardial ischemia, vein insufficiency, progressive cardiac insufficiency after myocardial infarction, diabetic complication, diabetic retinopathy, diabetic nephropathy, nephritis, glomerulonephritis, arteriosclerosis, angiohypertrophy, vascular hypertrophy or obstruction after intervention, vascular reobstruction after bypass surgery, hyperaldosteronism, glomerulosclerosis, renal insufficiency, glaucoma, intraocular high tension, hyperlipemia, angina pectoris, aneurysm, coronary arteriosclerosis, cerebral arteriosclerosis, peripheral arteriosclerosis, thrombosis, disease of central nervous system, Alzheimer's disease, deficiency of memory, depression, amnesia, senile dementia, sensory disturbances, multiple system organ failure, a disease due to endothelial dysfunction or scleroderma, or the prevention or amelioration of anxiety neurosis, catatonia, indisposition or dyspeptic symptoms.

* * * * *